United States Patent
Jia et al.

(10) Patent No.: US 11,229,392 B2
(45) Date of Patent: Jan. 25, 2022

(54) DETECTION AND LOCALIZATION OF CARDIAC FAST FIRING

(71) Applicant: CARDIOINSIGHT TECHNOLOGIES, INC., Independence, OH (US)

(72) Inventors: Ping Jia, Solon, OH (US); Qingguo Zeng, Solon, OH (US); Timothy G. Laske, Shoreview, MN (US); Qing Lou, Powell, OH (US)

(73) Assignee: CARDIOINSIGHT TECHNOLOGIES, INC., Independence, OH (US)

( * ) Notice: Subject to any disclaimer, the term of this patent is extended or adjusted under 35 U.S.C. 154(b) by 122 days.

(21) Appl. No.: 16/353,534

(22) Filed: Mar. 14, 2019

(65) Prior Publication Data

US 2019/0282112 A1    Sep. 19, 2019

Related U.S. Application Data

(60) Provisional application No. 62/643,456, filed on Mar. 15, 2018.

(51) Int. Cl.
*A61B 5/04* (2006.01)
*A61B 5/316* (2021.01)
(Continued)

(52) U.S. Cl.
CPC .............. *A61B 5/316* (2021.01); *A61B 5/282* (2021.01); *A61B 5/287* (2021.01); *A61B 5/349* (2021.01);
(Continued)

(58) Field of Classification Search
CPC .................................................. A61B 5/04085
See application file for complete search history.

(56) References Cited

U.S. PATENT DOCUMENTS

| 5,046,504 A | 9/1991 | Albert et al. |
| 9,427,166 B2 | 8/2016 | Dubois et al. |
| (Continued) | | |

FOREIGN PATENT DOCUMENTS

| EP | 1300110 A2 | 4/2003 |
| WO | 2008/035070 A2 | 3/2008 |

OTHER PUBLICATIONS

Sanders et al. Spectral Analysis Identifies Sites of High-Frequency Activity Maintaining Atrial Fibrillation in Humans, 2005, Circulation, 112:789-797. (Year: 2005).*

(Continued)

*Primary Examiner* — Rex R Holmes
*Assistant Examiner* — Jennifer L Ghand
(74) *Attorney, Agent, or Firm* — Tarolli, Sundheim, Covell & Tummino LLP

(57) ABSTRACT

Systems and methods for cardiac fast firing (e.g., atrial fast firing) detection perform frequency analysis on channels of collected cardiac waveform data and test the data for outlier frequency complex content that is of higher frequency than baseline frequency complex content associated with cardiac fibrillation (e.g., atrial fibrillation) or other arrhythmogenic activity. Anatomical regions from whence the cardiac fast firing originates can be displayed in real time on an epicardial surface map via a graphical display, aiding administration of therapy. Prior to such detection, QRST complex removal can be performed to ensure that ventricular activity (Continued)

does not infect the atrial fast firing analysis. A frequency-based method for QRST complex removal is also disclosed.

22 Claims, 20 Drawing Sheets

(51) Int. Cl.
    *A61B 5/00*     (2006.01)
    *A61B 5/35*     (2021.01)
    *A61B 5/282*     (2021.01)
    *A61B 5/287*     (2021.01)
    *A61B 5/349*     (2021.01)
    *A61B 5/361*     (2021.01)
    *A61B 5/363*     (2021.01)
    *A61B 5/339*     (2021.01)

(52) U.S. Cl.
    CPC ............ *A61B 5/35* (2021.01); *A61B 5/361* (2021.01); *A61B 5/363* (2021.01); *A61B 5/6805* (2013.01); *A61B 5/7246* (2013.01); *A61B 5/7257* (2013.01); *A61B 5/7282* (2013.01); *A61B 5/0006* (2013.01); *A61B 5/339* (2021.01)

(56) References Cited

U.S. PATENT DOCUMENTS

| | | | |
|---|---|---|---|
| 2002/0058870 A1 | 5/2002 | Panescu et al. | |
| 2014/0088395 A1* | 3/2014 | Dubois | A61B 5/046 600/382 |
| 2014/0336520 A1* | 11/2014 | Zeng | A61N 7/00 600/516 |
| 2016/0058369 A1* | 3/2016 | Bokan | A61B 5/743 600/424 |
| 2017/0055864 A1* | 3/2017 | Han | A61B 5/04011 |
| 2017/0319089 A1* | 11/2017 | Lou | A61B 5/0472 |

OTHER PUBLICATIONS

Nitish V Thakor, et al.: "Estimation of QRS Complex Power Spectra for Design of a QRS Filter", IEEE Transactions on Biomedical Engineering, IEEE Service Center, Piscataway, NJ, USA, vol. BME-19, No. 11, Nov. 1, 1984 (Nov. 1, 1984), pp. 702-706, XP011173564, ISSN: 0018-9294.

Applicant: Cardioinsight Technologies, Inc.; International PCT Application No. PCT/US2019/022290; Filed: Mar. 14, 2019; PCT International Search Report and PCT Written Opinion; Authorized Officer: Wolfgang Meyer; Date of Completion: May 21, 2019; 15 pgs.

* cited by examiner

DETECTION AND LOCALIZATION OF CARDIAC FAST FIRING

RELATED APPLICATION

This application claims the benefit of priority from U.S. provisional patent application No. 62/643,456, filed Mar. 15, 2018, entitled DETECTION AND LOCALIZATION OF CARDIAC FAST FIRING, which is incorporated herein by reference in its entirety.

TECHNICAL FIELD

This disclosure relates to detection and analysis of cardiac waveforms.

BACKGROUND

An electrocardiogram (ECG) system monitors electrical activity of a heart of a patient via invasive or external electrodes. An electrophysiology (EP) procedure uses single or multiple catheters within the heart to assess the electrical activity and conduction pathways of the heart.

SUMMARY

This disclosure relates to detection and analysis of cardiac waveforms.

As one example, a method of real-time detection of cardiac fast firing activity includes collecting cardiac waveform data from a plurality of channels. For the example of detecting atrial fast firing activity, QRST content can be removed from each channel of the collected cardiac waveform. A frequency analysis is performed for each channel over a moving window. Channels exhibiting a fast-firing frequency peak during a particular window are identified. Channels identified as fast-firing in a particular time frame are mapped to one or more epicardial surface regions, and a graphical output indicative of the time and epicardial location of fast-firing activity is provided.

As another example, a system includes a processor and non-transitory memory to store electrical data representing a plurality of ECG signals and machine-readable instructions. The processor accesses the non-transitory memory and executes the machine-readable instructions. The instructions include cardiac fast firing detection code programmed to perform cardiac fast firing detection to determine outlier dominant frequencies for a plurality of ECG signals. Code is also programmed to store in the memory cardiac fast firing data to specify times, channels, and/or epicardial surface regions exhibiting cardiac fast firing. A display visualizes a graphical representation based on the cardiac fast firing data.

As yet another example, a method may include frequency-domain removal of QRST complexes from cardiac waveform signals.

DETAILED DESCRIPTION

Figure 1:
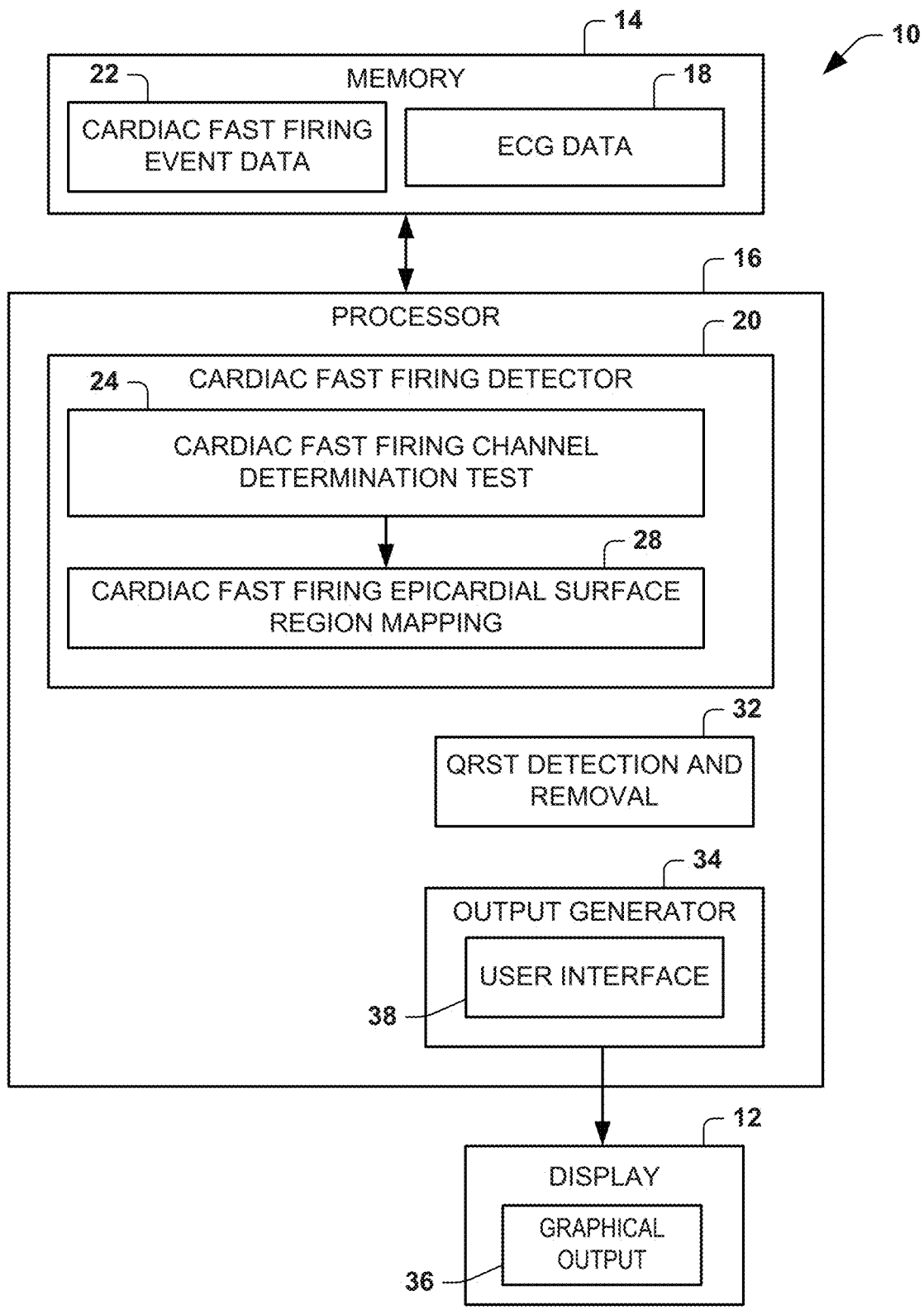
FIG. 1 depicts an example system to detect and analyze cardiac waveforms and to perform cardiac fast firing detection.

Cardiac fast firing refers to anomalous cardiac electrical activity that is higher in frequency than that associated with fibrillatory activity such as atrial fibrillation and ventricular fibrillation. An example of cardiac fast firing is atrial fast firing, which is an electrophysiological signal that originates in the atrium, and is faster than the rest of the atrial chambers. Cardiac fast firing can occur in brief episodes lasting a time interval of only a few seconds, and each episode is localized to one contiguous region of the heart (or multiple separate regions of the heart) as opposed to being evident across the entire cardiac surface. Detection of cardiac fast firing therefore in part involves looking for outlier frequency activity generally in a predetermined frequency range (e.g., about 8-15 Hz) and, where detected using body surface measurements (BSM) of cardiac electrical activity, amongst only a subset of BSM channels, e.g., ECG channels. Some patients may exhibit very fast baseline cardiac activity, e.g., very fast baseline atrial activity, meaning that the outlier activity indicative of cardiac fast firing (e.g., atrial fast firing) may be found for such patients in a higher frequency range (e.g., about 10-15 Hz). The precise demarcation between cardiac fast firing and baseline fibrillation activity may vary from patient to patient.

Detection and localization of the anatomical origination of cardiac fast firing activity is of clinical significance, such as presenting one or more potential targets for ablation or other treatments to correct or mitigate cardiac dysfunction. Detection and localization of cardiac fast firing episodes can therefore be consequential to patient treatment by permitting a targeted therapy to be delivered while a patient is undergoing an EP procedure, for example. Such detection and localization can also be used as a screener to prompt further diagnostic investigation. The detection and localization may be implemented in an offline analysis or in real time. By "real time," it is meant that a cardiac fast firing event is detected and localized within seconds of the occurrence of the event, as opposed to, for example, during later offline analysis of collected data performed substantially after the collection of such data, e.g., minutes or hours afterward.

This disclosure relates to detection and analysis of cardiac waveforms, including detecting cardiac fast firing, and in some examples doing so in real time. The detection and analysis can also include detection and removal of QRST complexes from cardiac waveforms to improve atrial fast firing detection. The detected waveforms and associated analysis further can be used to drive an output to a display corresponding to an interactive graphical map (e.g., a graphical user interface (GUI)). The GUI can, for example, alert a physician to one or more detected fast-firing events and/or can display one or more graphical maps, corresponding, for example, to the thorax and/or to the epicardial surface, indicating either or both of the body surface location or the cardiac location of the detected fast firing, which can then serve as a guide to an ablation procedure, for example, in order to correct or mitigate faulty cardiac functioning.

As used herein, an "electrocardiogram signal" ("ECG signal") refers to a graph of voltage over time recorded for one or more channels each based on a cardiac electrical signal sensed by an electrode. ECG signals can be generated from body surface measurements (BSMs). The systems and methods described herein can display and highlight regions of interest (i.e., portions of the cardiac surface) corresponding to likely sources of fast firing electrical activity, and thus to potential treatment targets, without needing to display ECG signals, reconstruct electrograms on the heart surface from the ECG signals, or generating a cycle length map or a dominant frequency map. The present systems and methods thus obviate the need for an operator to manually select any particular beat for analysis, because the systems and methods can automatically and contemporaneously process continuously collected ECG signals to produce graphical display outputs illustrating fast-firing cardiac surface regions, all of which can be done in real time. By contrast, systems and methods that rely on solving the inverse problem to reconstruct electrograms on the heart surface can require conscious and deliberate operator choice of a beat for reconstruction. In some examples, however, the ECG signals can be used to reconstruct electrograms on a cardiac envelope that are computed by solving an inverse problem based on electrical signals acquired from a set of non-invasive body surface measurements and geometry data that relates the body surface measurement locations with respect to the cardiac envelope.

In some examples, a computed tomography (CT) scan of the patient can be performed to build a heart and torso geometrical relationship in the form of a transfer matrix A. From the transfer matrix A, an inverse transfer matrix $A^{-1}$, which can also be called the influence coefficient matrix, can be calculated. Real time methods of calculating the inverse transfer matrix $A^{-1}$ are described in U.S. Pat. No. 9,256,166 to Rudy et al., which is herein incorporated by reference. This inverse transfer matrix $A^{-1}$ defines the influence of each electrode position on each cardiac surface location. The inverse transfer matrix $A^{-1}$ is a matching table in itself, providing a correspondence between body surface measurement (BSM) channels (e.g., from electrodes on a vest) and cardiac surface locations, in other words, a torso-heart relationship relating the contribution of electrical activity from each location on the heart to the potentials measured at each location on the torso and thus to each individual BSM channel. Then, the subset of BSM channels that exhibit an outlier component in the high-frequency spectrum can be determined. This determined subset of BSM channels can be said to be fast-firing channels. The columns in the inverse transfer matrix $A^{-1}$ corresponding to the determined fast-firing channels can then be examined to determine the absolute-value largest coefficient, or several such coefficients, in each of said columns. Said absolute-value largest coefficients correspond to the cardiac surface locations having the largest contributions to their respective BSM channels. The particular columns examined in the inverse transfer matrix $A^{-1}$ can thus be limited to those corresponding to channels in which fast-firing activity is detected. There can then be generated a graphical representation of the cardiac surface, or a region of interest of the cardiac surface, highlighting the particular locations, as determined from the examination of the fast-firing channel columns in the inverse transfer matrix $A^{-1}$, to find the largest coefficients in each. This generated graphical representation is indicative of the location of fast-firing activity.

Systems and methods described herein are thus capable of "mapping" a few selected ECG channels, corresponding, for example, to certain ECG electrodes in a vest having many such electrodes, to corresponding cardiac surface locations, such as by determining the largest influential cardiac locations in the inverse transfer matrix $A^{-1}$. The selected (e.g., vest) channels can be identified by high frequency components in their ECG signals. Thus, the selected (e.g., vest) channels with high frequency components can be "mapped" to locations on the heart surface to generate, e.g., graphical depictions indicative of likely locations of the origination of detected fast firing. More discussion of the relationship between BSM channels and cardiac surface locations may be found in, for example, U.S. Pat. No. 9,549,683 to Jia et al. and U.S. Pat. No. 9,186,515 to Ramanathan et al., which patents are herein incorporated by reference.

FIG. 1 depicts an example of a system 10 to detect and analyze cardiac fast firing as well as to generate graphical maps indicative of the locations of the detected cardiac fast firing that can be visualized on a display 12. The system 10 includes memory 14, which can include one or more non-transitory machine-readable media. The system 10 also includes a processor 16, which can include one or more processing cores, to access the memory and execute corresponding instructions demonstrated within the processor block 16.

In the example of FIG. 1, the memory 14 stores electrophysiological (e.g., ECG) data 18. In some examples, the ECG data 18 corresponds to raw (e.g., unfiltered and preprocessed) ECG signals that are measured non-invasively via sensors placed on an outer surface of the patient's body (e.g., an arrangement of body surface sensors distributed non-invasively across an outer surface of a patient's body, such as the patient's thorax or a portion thereof, e.g., two hundred fifty-two sensors distributed approximately evenly about the thorax). Various measurement systems (not shown in FIG. 1, but see measurement system 566) can be used to acquire the body surface electrical measurements that can be utilized to provide the ECG data 18 that can either correspond to live data that is acquired at the time of implementing this method, or the ECG data 18 can correspond to data that has been acquired a priori, such as part of a previous electrophysiology (EP) procedure or acquired during another intervention.

The processor 16 executes machine readable instructions that include a cardiac fast firing detector 20 to detect cardiac fast firing events in ECG data 18. As an example, the cardiac fast firing detector 20 processes raw (e.g., non-line filtered) ECG data 18 for one or more selected time intervals of each of the plurality of input channels. The cardiac fast firing detector 20 employs frequency-based methods to identify fast firing episodes and to localize them to certain recording channels and/or to corresponding locations on the epicardial surface. The determined cardiac fast firing times and locations can be stored in memory as cardiac fast firing event data 22 specifying time stamps (indices), channels, epicardial surface regions, or other tags for cardiac fast firing events determined via the cardiac fast firing detector 20.

As a further example, the cardiac fast firing detector 20 includes cardiac fast firing channel determination code 24, which can utilize one or more tests for determining whether a channel exhibits cardiac fast firing activity during a time period, as described herein. The cardiac fast firing determination code 24 can perform frequency analysis on data from signal collection channels. As examples, the cardiac fast firing channel determination code 24 can employ statistical analysis of a composite signal, can perform single-channel temporal detection, or can perform multi-channel spatial detection to determine, that a cardiac fast firing episode has taken place and to isolate each of the channels exhibiting the cardiac fast firing activity.

The cardiac fast firing detector 20 also includes a mapping function 28 to map channels determined to exhibit cardiac fast firing activity to epicardial surface regions in order to graphically indicate the anatomical origin of cardiac fast firing events. For example, the mapping function 28 can use the largest (absolute-value) influence coefficients in the inverse transfer matrix $A^{-1}$ to detect anatomical regions that are the source of fast firing, in some examples in real time, as soon as the fast firing is detected in certain body surface (e.g., vest) channels.

As a further example, the processor 16 can also execute instructions corresponding to QRST detection and removal function 32 when the system 10 is configured to detect atrial fast firing. The QRST detection and removal function 32 processes the ECG data signals across channels to remove ventricular signal components to facilitate analysis of atrial signals, including the cardiac fast firing detector. The QRST detection and removal function 32 can, for example, generate a QRST template that combines QRS complex and T wave into a single template region of interest.

For example, the QRST detection and removal function 32 can perform principal component analysis (PCA) on a region of interest of a cardiac waveform, such as can be selected automatically or manually in response to a user input identifying an interval of signal corresponding to QRST complex. The PCA can thus be used to generate a QRST template definition that can be applied across the time frames, such as by time stepping the template with respect to ECG data to be searched to determine correlation coefficients. The peak correlation coefficients are used to identify potential locations in which the template matches the data. The correlation coefficients can be compared to a threshold to identify corresponding regions of interest for each of a plurality of channels.

The QRST detection and removal function 32 can remove each region of interest (i.e., each corresponding to a QRST complex) and perform spline interpolation to automatically connect adjacent P waves. As an example, the interpolation can be implemented as a shape-preserving piecewise cubic interpolation (e.g., piecewise cubic Hermite interpolating polynomial (PCHIP) or another spline interpolation function). Such an interpolation function keeps the interpolated values monotonic (e.g., either increasing or decreasing) based on the ending point values used for such interpolation. The QRST complex is thereby replaced in the cardiac waveform being analyzed with a substitute signal portion having no high-frequency content that would interfere with analysis of the waveform for other purposes. The processor 16 can also implement baseline removal and/or remove bad input channels prior to executing the QRST detection and removal function 32, such as disclosed herein.

As another example, the QRST detection and removal function 32 can use a frequency-based method to remove frequency content associated with QRST complexes from the frequency analysis plot for each channel. For example, a fast Fourier transform may be applied to ECG signals for each channel, and frequencies corresponding QRST complexes may be removed from each frequency-domain ECG signal. Processor 16 can be configured to remove QRST complexes prior to cardiac fast firing detection by detector 20.

An output generator 34 can be utilized to generate one or more graphical outputs 36 that can be presented on the display 12. For example, the output generator 34 can display a plurality of ECG signals, such as can be acquired for a plurality of measurement locations distributed across a body surface (invasively or non-invasively) or derived from measurements of electrical activity over a surface of the patient's body (e.g., an external and/or internal surface), such as disclosed herein. The output can also include graphical, text, or audible notifications or warnings indicative of the detection of cardiac fast firing and/or the time(s) of such fast firing.

The output generator 34 can also include a user interface 38 that can be utilized to set parameters for controlling which ECG signals are included in the output 36 in response to user input, and to otherwise interact with and select portions of the electrophysiological (e.g., ECG) data 18, such as disclosed herein. For example, the user interface 38 can be used manually specify baseline frequency parameters for use in the cardiac fast firing detection. As another example, the user interface 38 can be used to manually specify a portion of a cardiac waveform to use as a QRST template for use in the QRST detection and removal process. For specifying such a portion, the output generator 34 can generate a set of calipers that are placed at the start and stop times of a selected interval.

The output generator 34 can also generate one or more electrophysiological maps in the graphical output 36 that can be presented on the display 12. For example, the output generator 34 can generate an activation map or other map representing arrhythmogenic activity, such as based on the channels following QRST removal. This can be for a selected set of the signals distributed across the surface or for the entire surface and for one or more time intervals of interest, which can be selected in response to a user input. Examples of the types of output visualizations and maps that can be generated may be found in U.S. Pat. No. 9,427,169 and/or U.S. patent application publication No. 2014/0200822. The output can also include a graphical map illustrating channels from which fast firing events were detected. The output can also include a graphical representation of a region of the cardiac surface showing the estimated or determined location of origin of a cardiac fast firing event.

As disclosed herein, in some examples, the ECG data 18 is spatially and temporally consistent across the entire surface on which the ECG signals were measured or derived. As a result, the ECG signals can be generated for the entire cardiac surface over one or more time intervals. The output generator 34 can employ the user interface to set parameters for the graphical map and to otherwise interact with and select portions of the electrophysiological data 18 in response to user input, such as disclosed herein.

Data Collection for Cardiac Fast Firing Detection

While the cardiac fast firing detection of the present application does not require that an EP procedure be performed, uses of the described cardiac fast firing detection can take place in the context of an EP procedure or a similar diagnostic or therapeutic procedure. An EP procedure or like procedure generally involves, first, a period of patient and physician preparation during which the patient is prepped for the procedure and the physicians involved perform catheter insertion and/or other preparations; second, the procedure proper, during which measurements may be taken and therapies (e.g., cardiac ablations or drug deliveries) may be applied; and third, a resting period following the procedure during which the patient remains to rest and be observed, and during which data can continue to be collected. Prior to the procedure the patient may be outfitted with an array of cardiac sensors such as electrophysiological sensors, which may, for example, be applied as a vest such that a plurality of such sensors are distributed over the thoracic surface. As an example, more than one hundred sensors (e.g., two hundred fifty-two sensors) can be applied. In other examples, different numbers and arrangements of sensors may be used, such as an arrangement of electrodes configured to sense cardiac electrical activity. Signals collected by the applied sensors can be monitored and analyzed for cardiac fast firing at any of the above-described phases of the procedure.

Cardiac Fast Firing Detection

Figure 2:
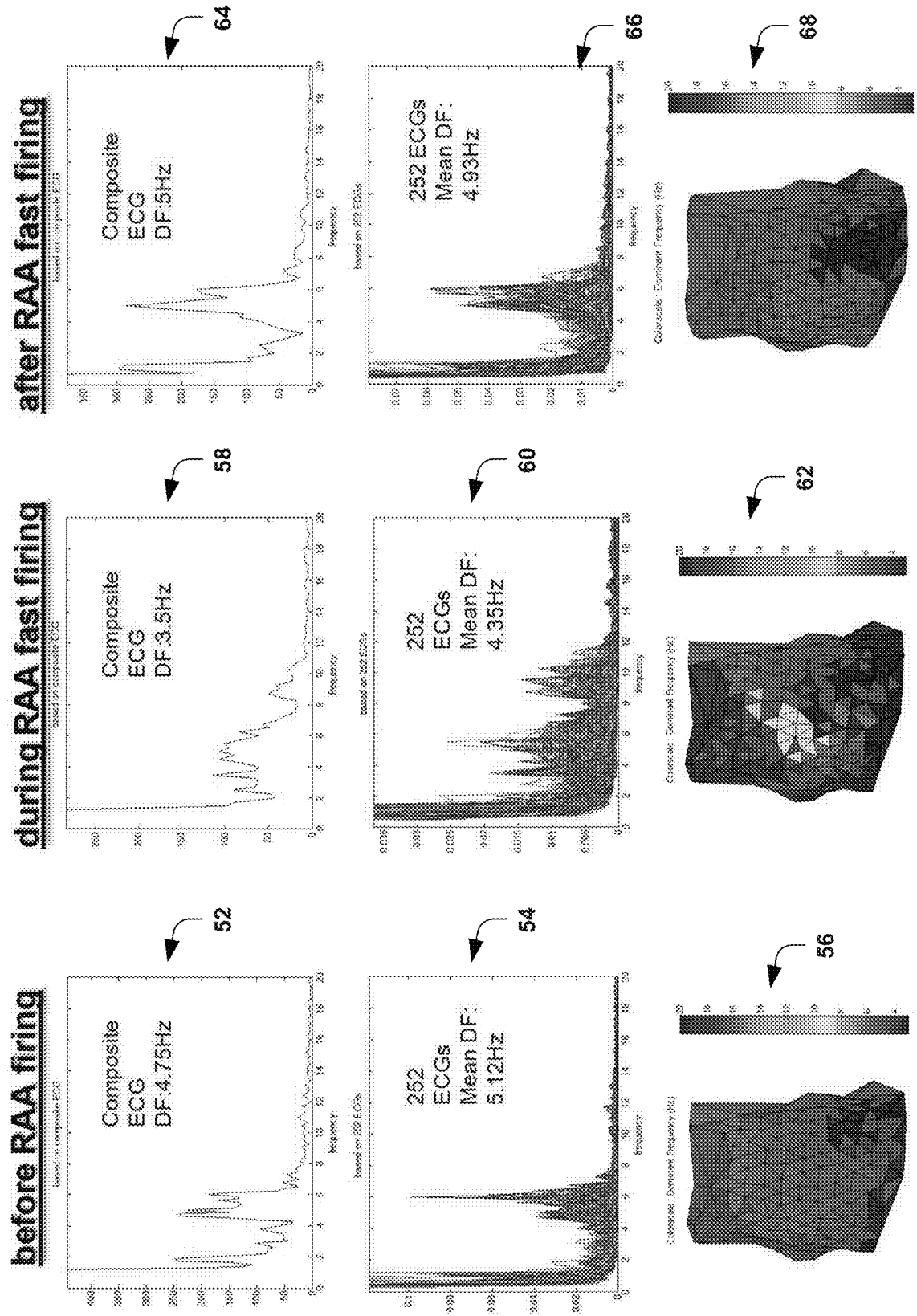
FIG. 2 illustrates examples of frequency analysis plots and thoracic channel location graphical representations used in cardiac fast firing detection.
Figure 3B:
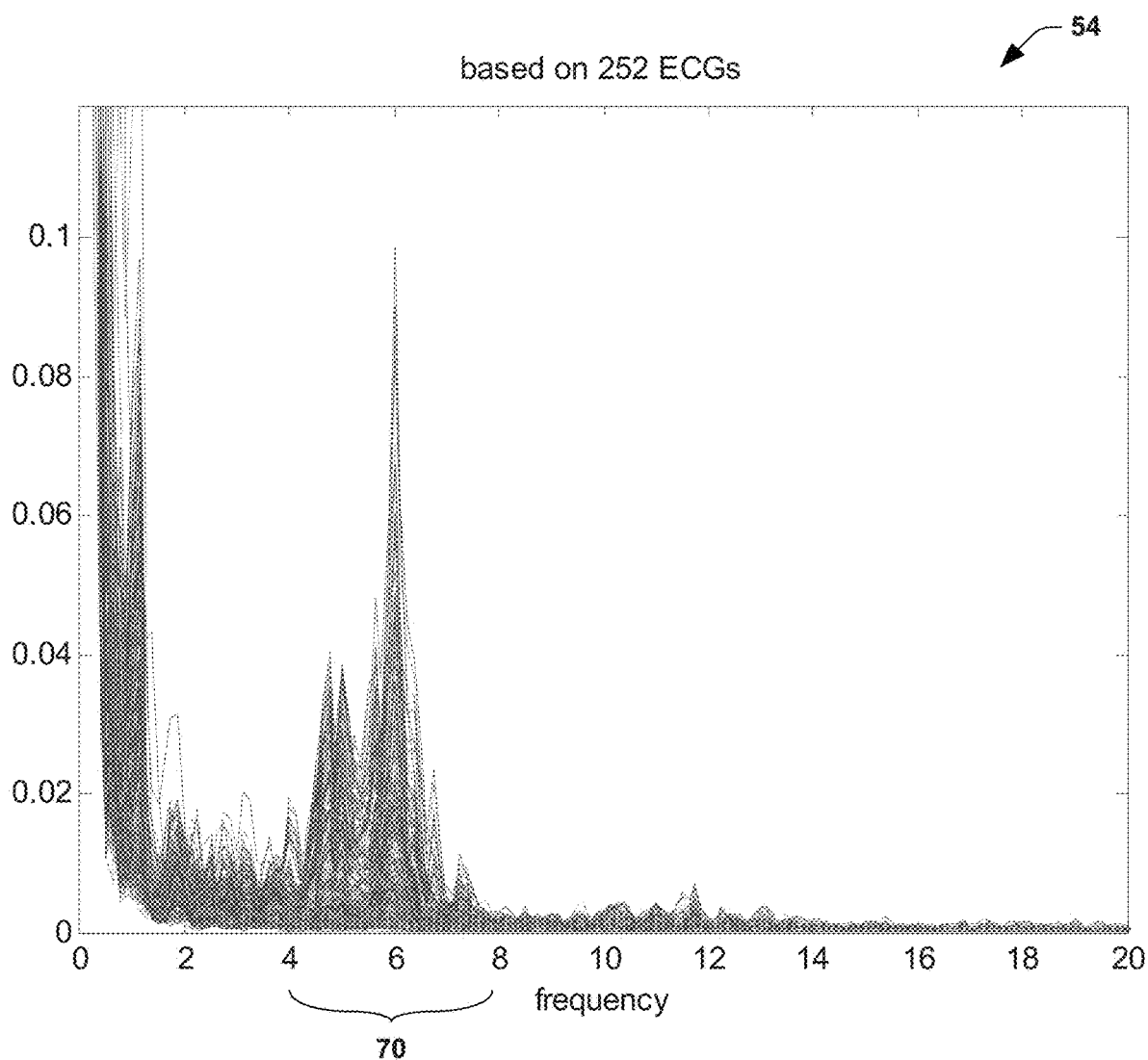

FIG. 2 depicts an example overview of a first part of a cardiac fast firing detection method, corresponding to the functioning of cardiac fast firing detector 20 of FIG. 1. The middle row of FIG. 2 shows three power graphs 54, 60, 66, each of which is illustrated in a larger version in FIGS. 3B, 4B, and 5B, respectively. Power graphs 54, 60, 66 respectively illustrate examples of fast firing activity from a windowed segment of collected electrophysiological data before, during, and after a detected fast firing event originating in the right atrial appendage (RAA). Each graph 54, 60, 66 contains numerous frequency plots (e.g., about 252 plots), one plot per electrophysiological channel, each plot corresponding to the frequency spectrum of a cardiac waveform measured from a patient. Each frequency plot may be obtained, for example, by taking the fast Fourier transform (FFT) of a window of collected time-domain electrophysiological data; other frequency transforms may also suffice. The length of the window may be chosen to be, for example, two seconds, five seconds, ten seconds, or twenty seconds. The frequency plots may have had QRST content (or, more specifically, ventricular QRST content) removed, for example, using one or more of the methods described herein so as to better present frequency content attributable solely to atrial electrical activity.

Figure 3A:
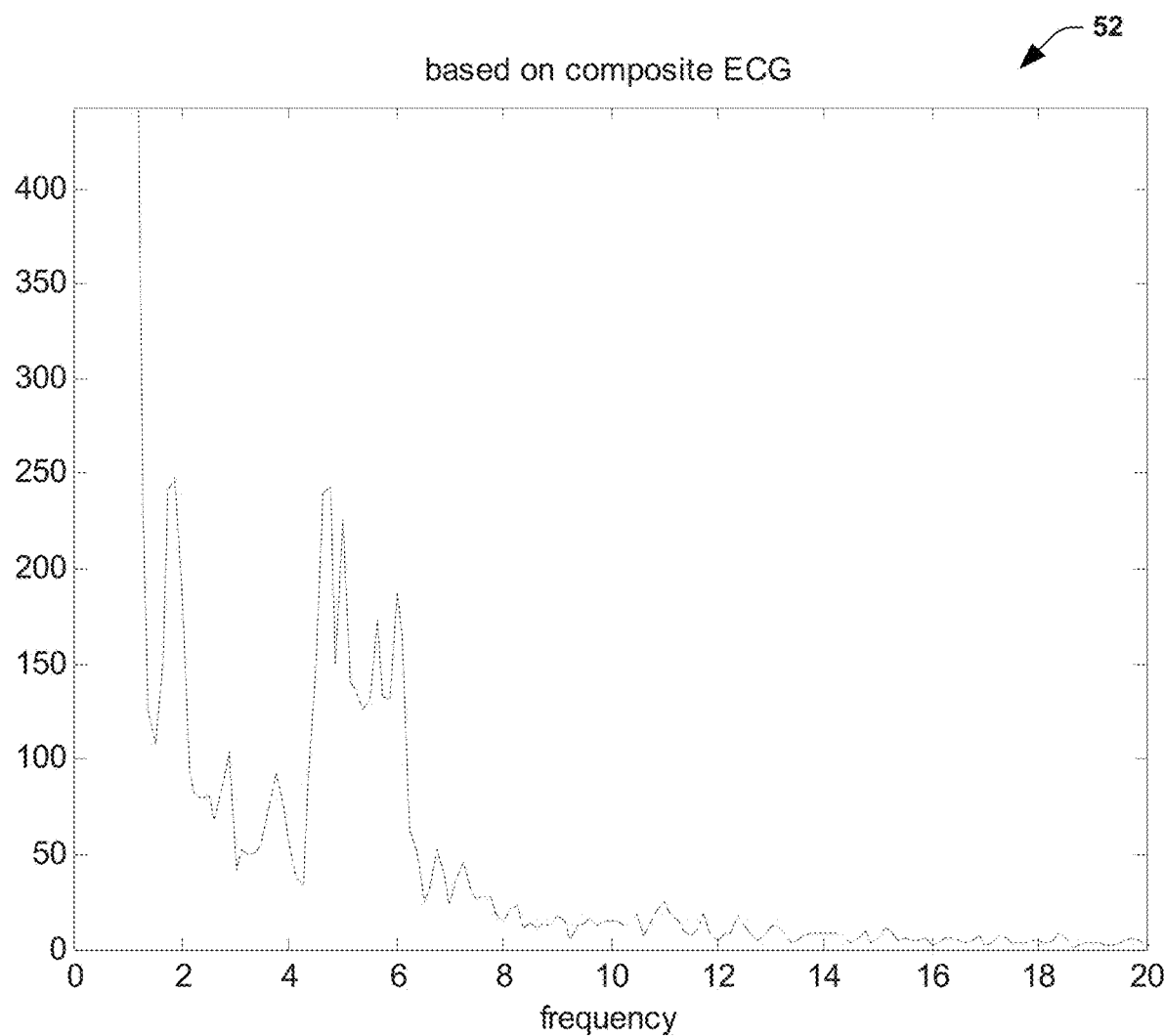
FIGS. 3A-3C, 4A-4C, and 5A-5C depict larger versions of the plots and representations of FIG. 2.
Figure 4A:
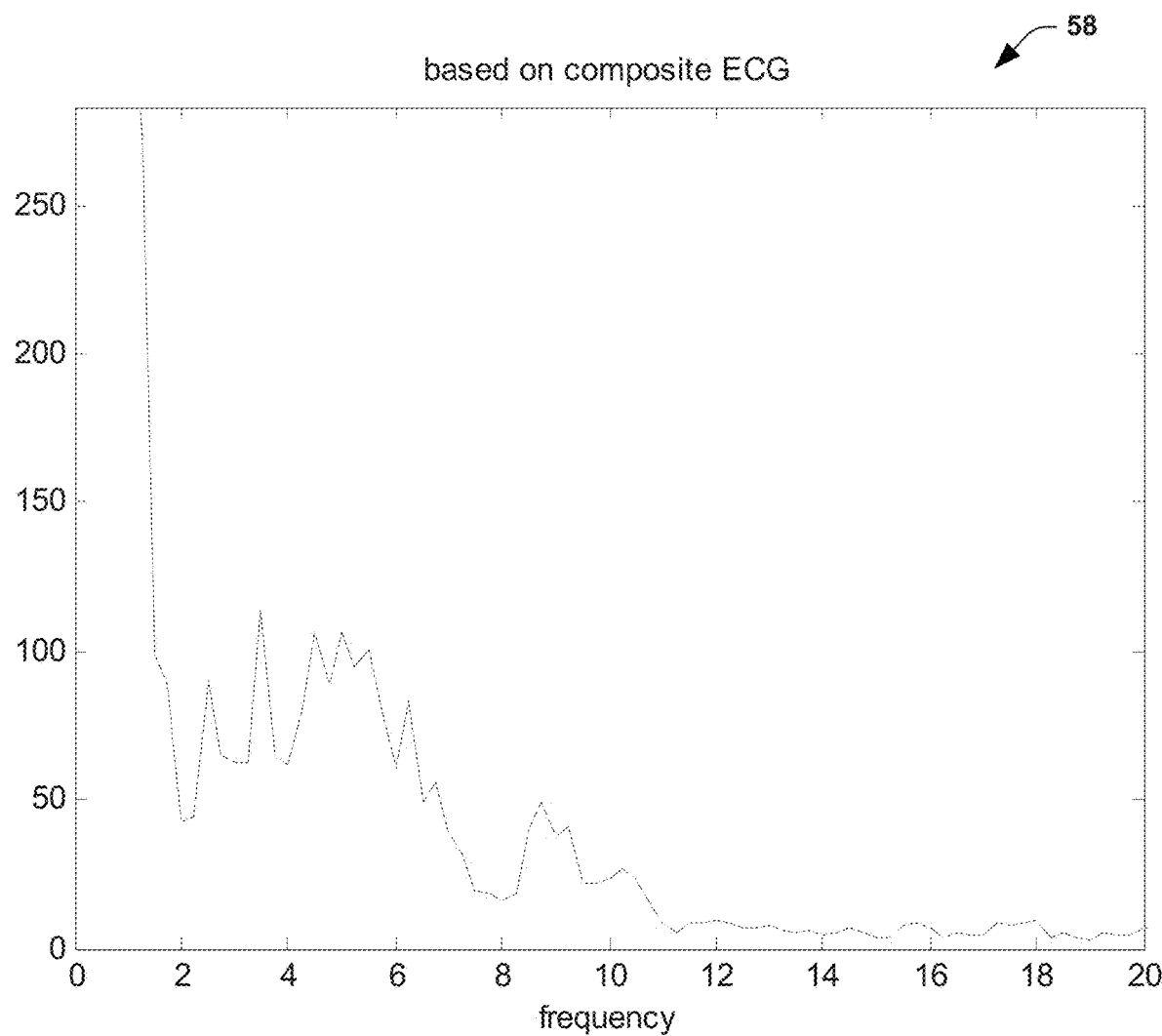
Figure 4B:
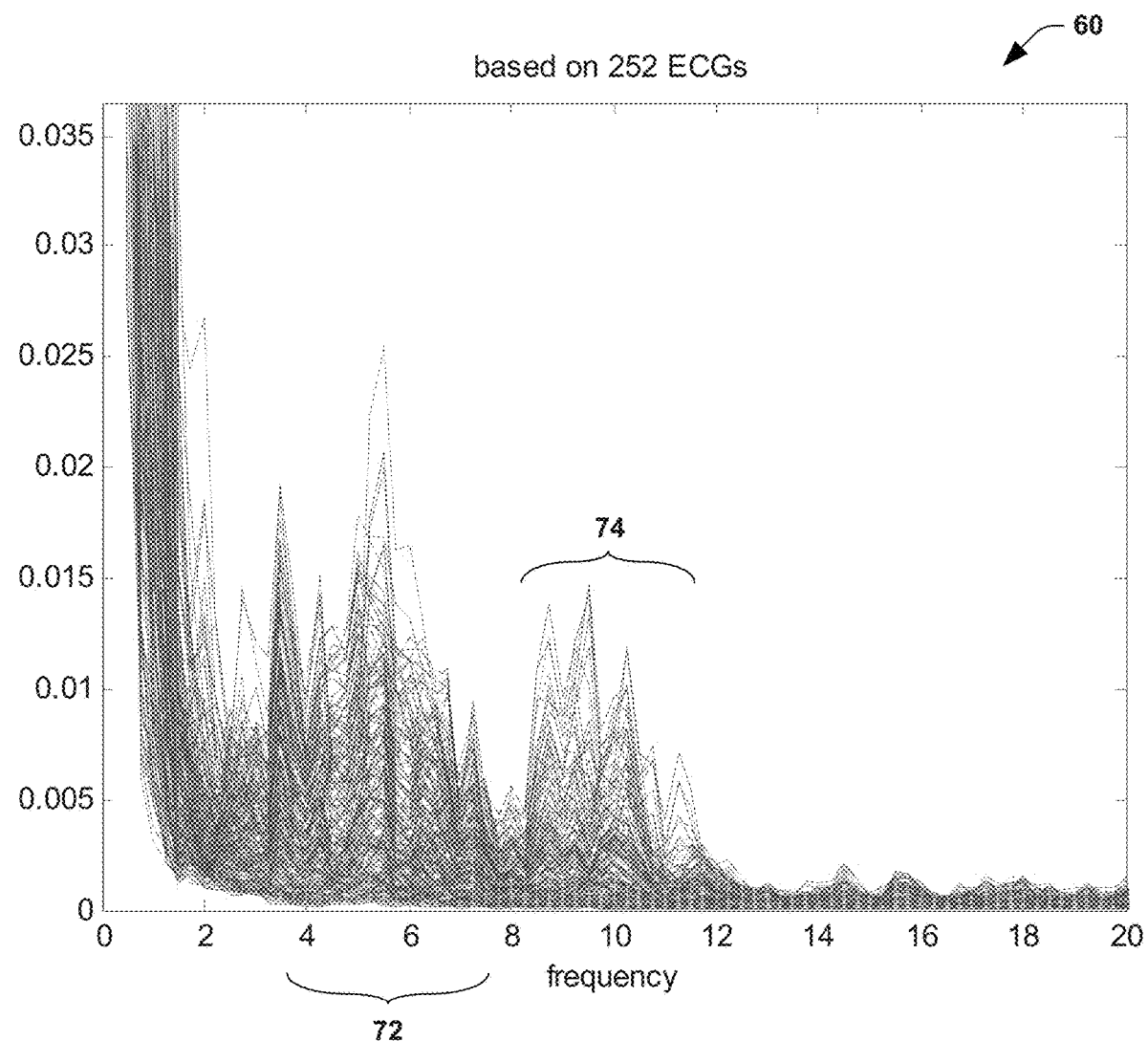
Figure 5A:
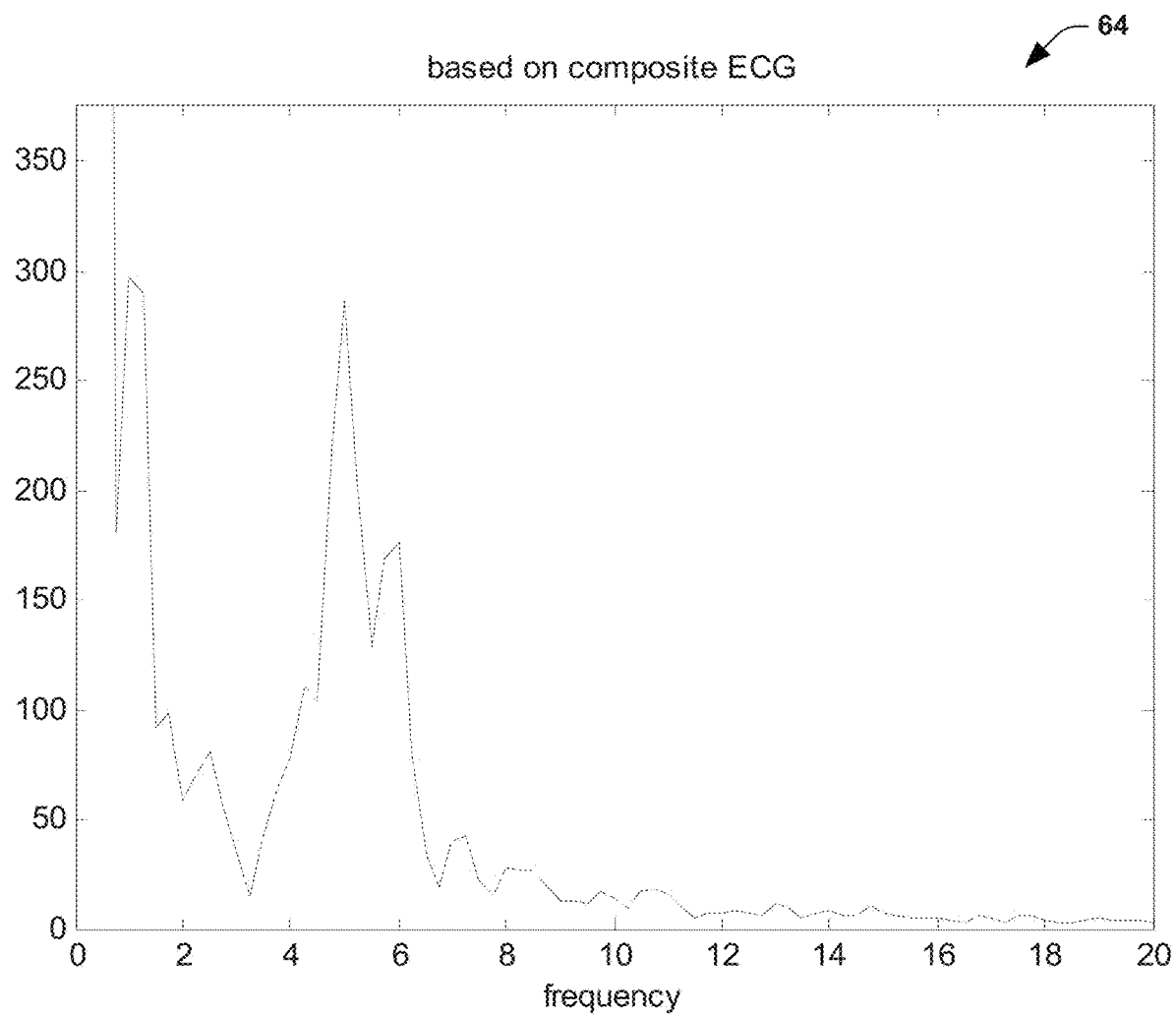
Figure 5B:
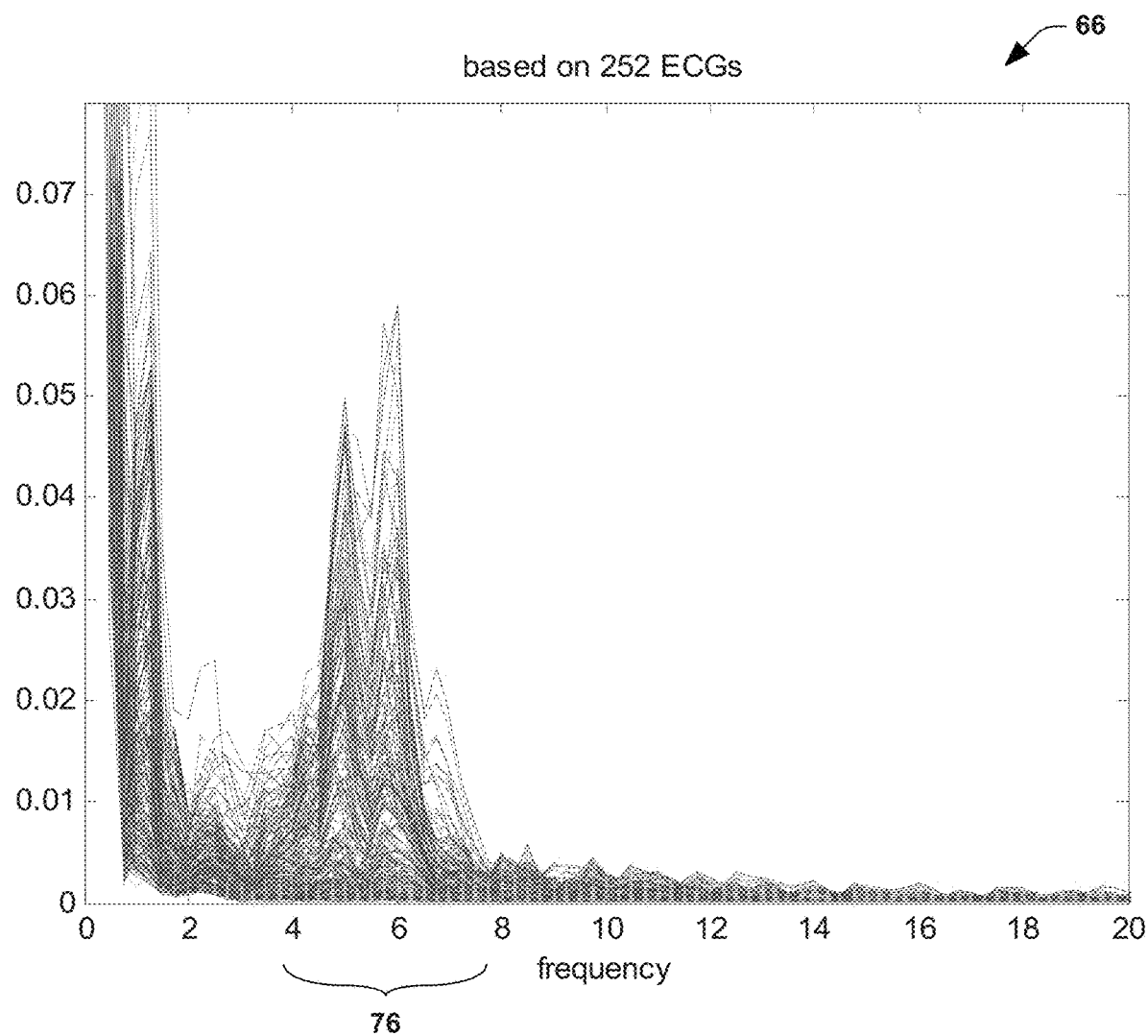

The upper row of FIG. 2 shows three graphs 52, 58, 64, each of which is a composite power spectrum derived from substantially all of the plots in respective graphs 54, 60, 66 in the middle row of FIG. 2. For example, graph 52 may be arrived at by summing all of the frequency plots of graph 54, or by taking an average, or by using any other suitable method for obtaining a composite; graphs 58 and 64 may be obtained similarly from graphs 60 and 66, respectively. Larger versions of graphs 52, 58, 64 are shown in FIGS. 3A, 4A, and 5A, respectively.

Figure 3C:
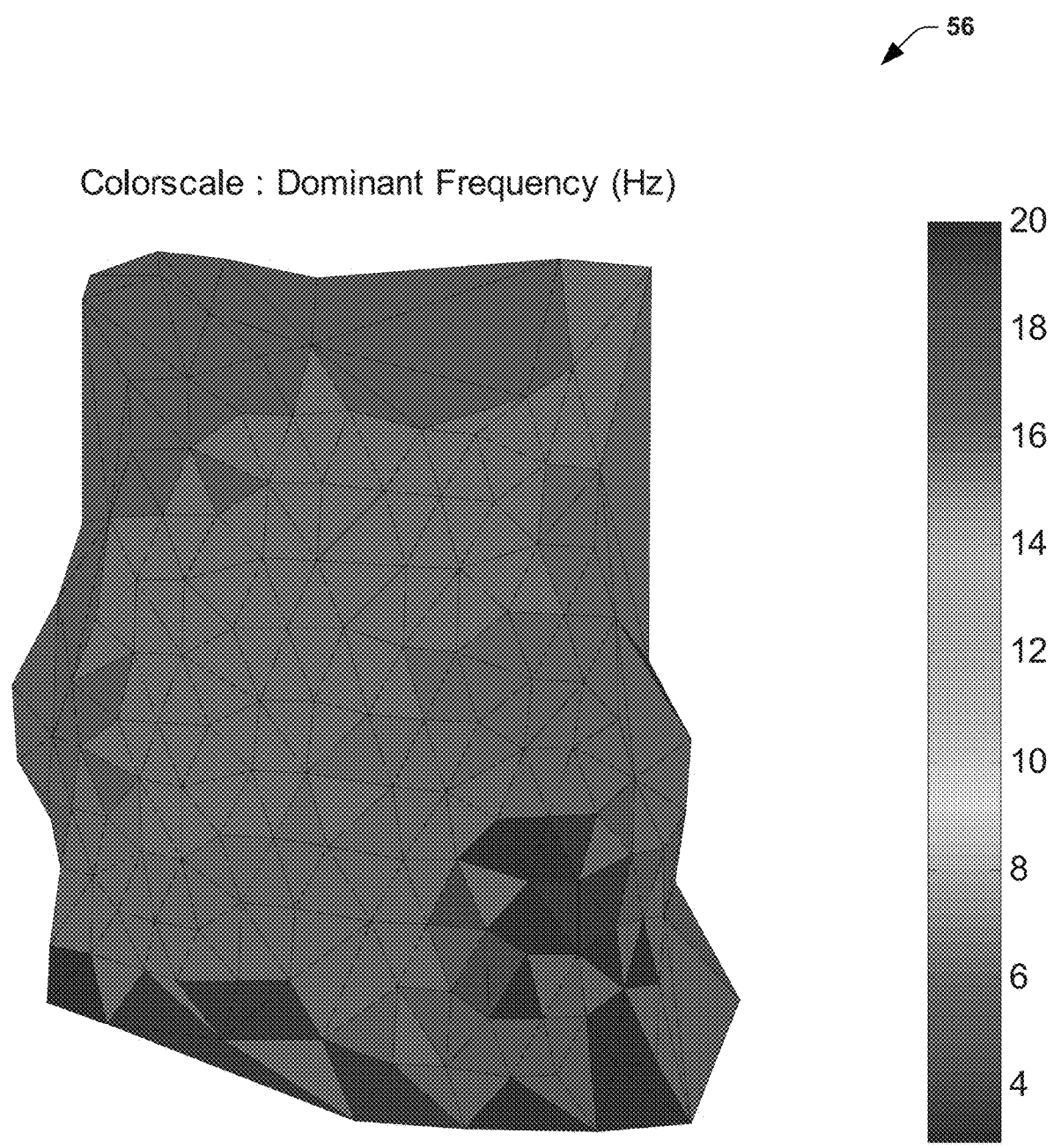
Figure 4C:
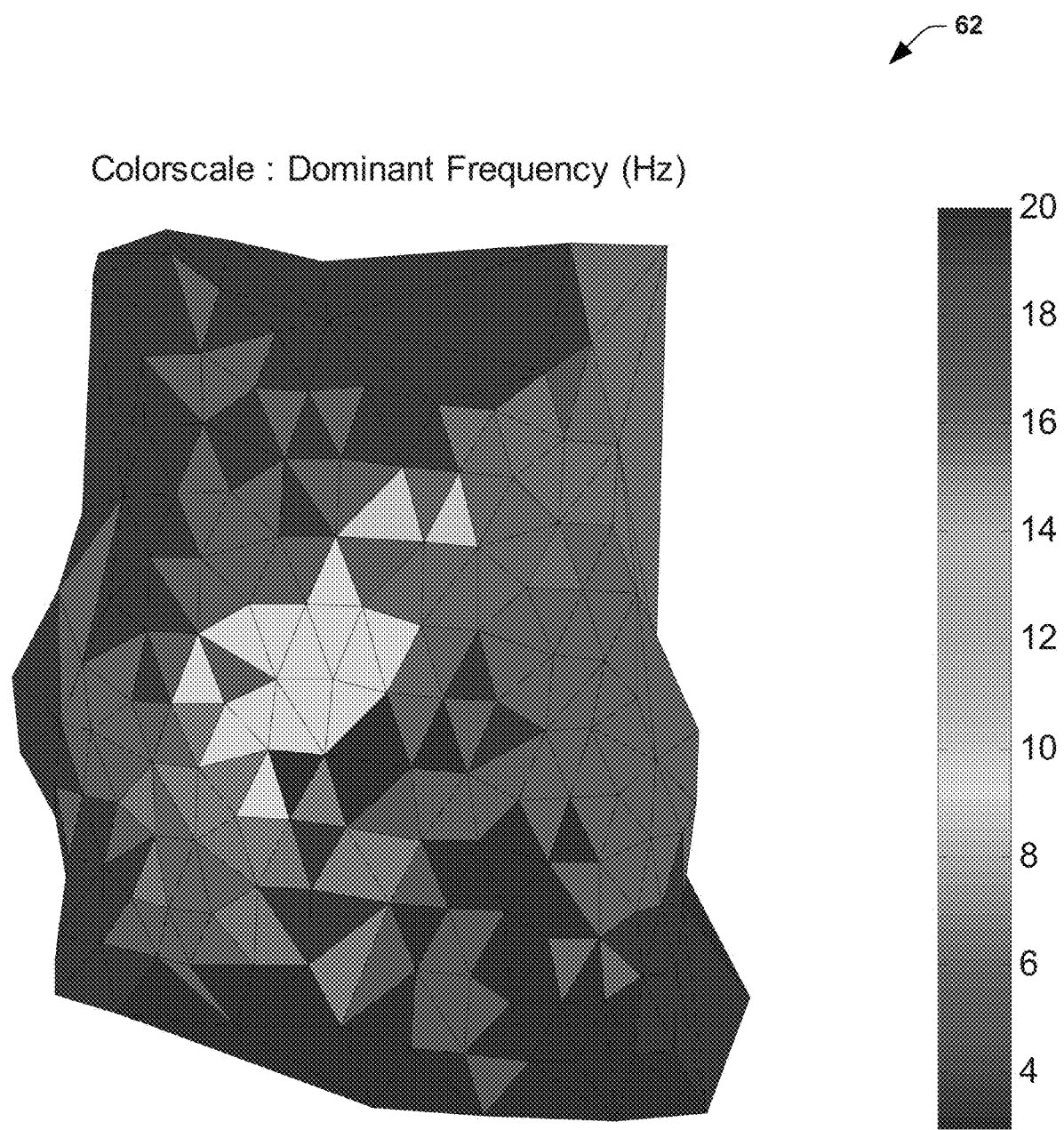
Figure 5C:
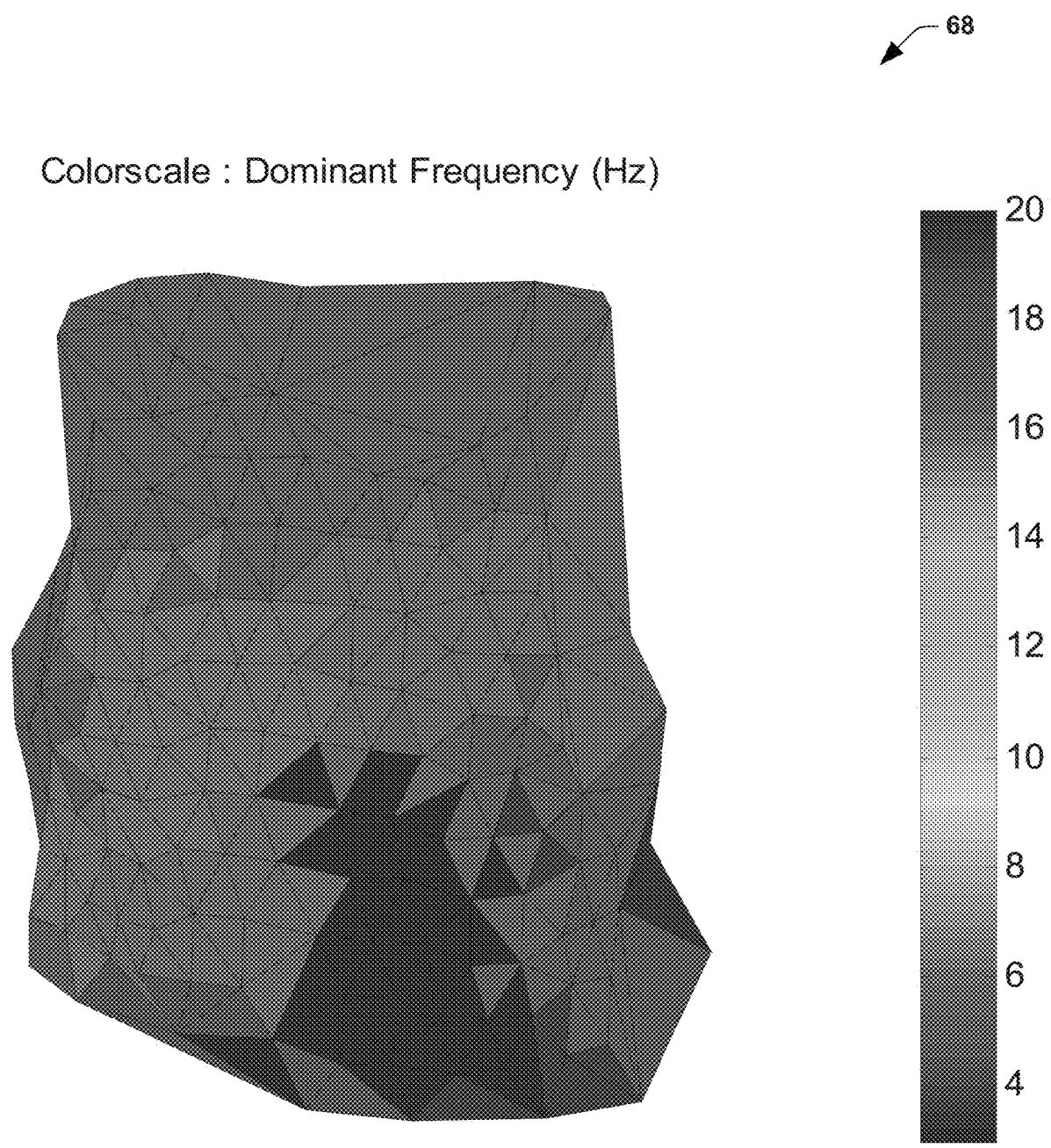

The lower row of FIG. 2 shows three graphical representations 56, 62, 68 of a patient thorax illustrating electrode distribution thereon, each triangle in each illustrated mesh corresponding to the position of an electrode among the set of electrodes used to obtain the electrophysiological data from which the middle and upper row graphs are obtained. Thus, each triangular surface face represents a channel used for data collection. Each triangle is shaded according to the dominant frequency of the corresponding channel. The lighter-shaded channels in graphical representation 62 are indicative of a detected fast-firing event. Larger versions of graphical representations 56, 62, 68 are shown in FIGS. 3C, 4C, and 5C, respectively.

As an example, the cardiac fast firing detection method of the present application involves performing a channel-by-channel frequency analysis on collected cardiac waveforms. Based on the frequency analysis, channels exhibiting a fast-firing frequency peak during a particular window can be identified. Said channels can then be mapped to one or more epicardial surface regions in order to localize the anatomical origin of cardiac fast firing. The fast firing determination (i.e., the binary determination that a fast-firing event has occurred), and/or times, channels, and/or anatomical regions associated with fast-firing events, can all be stored as cardiac fast firing event data 22 (in FIG. 1). The inputs to the cardiac fast firing detection method include the ECG data segments for a time interval, a list of bad channels (e.g., known disconnected channels, or channels exhibiting impedance too high to deliver useful data), and various input parameters, which can be manually or automatically defined.

In analyzing the frequency plots for any given time window for indications of fast-firing activity, all frequency content below about 2 Hz, which effectively corresponds to, for example, healthy cardiac activity and baseline wander, can be ignored. For a patient in atrial fibrillation, the remaining frequency content will generally show dominant frequencies of analyzed channels clustered in one or two frequency complexes. As shown in frequency analysis graph 54 of FIG. 2 or FIG. 3B, the majority of channels each have their respective dominant frequency peak in the 4-8 Hz range, constituting baseline complex 70, corresponding to fibrillatory cardiac activity (e.g., atrial fibrillation). The mean dominant frequency for all analyzed channels is 5.12 Hz in the illustrated example. The absence of a significant outlier frequency complex in graph 54 indicates that no fast-firing activity is detected in the analyzed time frame.

By contrast, frequency analysis graph 60 in FIG. 2, shown in larger form in FIG. 4B, which is from a later time frame than earlier graph 54, exhibits two major complexes 72, 74 of the frequency spectrum. In this example, in addition to 4-8 Hz baseline complex 72 during atrial fibrillation, a second, outlier complex 74, corresponding to atrial fast firing, is centered around 10 Hz. The detection of outlier complex 74 in a frequency range above that of previously established baseline complex 70 can trigger a warning that a fast-firing event has been detected and/or additional analysis to locate the anatomical origin of the fast firing event. One or more timestamps indicative of the time of the detected fast-firing activity can, for example, be stored in memory as event data 22 linked with the corresponding time-domain and/or frequency-domain ECG data. Frequency analysis graph 66 in FIG. 2, shown in larger form in FIG. 5B, again exhibits only one major frequency complex 76, indicating the cessation of the detected fast-firing event by the time of the analyzed time frame.

Cardiac fast-firing is characterized by outlier frequencies on a subset of channels (e.g., relatively few channels) showing such frequencies. Because cardiac fast-firing is a local event, it tends to be limited to a relatively small number of channels, e.g., about ten channels out of two hundred fifty-two channels in an array. In some examples, the outlier frequency cluster has, for example, a mean dominant frequency more than one standard deviation higher in frequency than the mean dominant frequency of the baseline cluster corresponding to fibrillatory cardiac activity, which may ignore low frequency content (e.g., sub-2 Hz frequency content). In other examples, other multiples of the standard deviation of the mean baseline frequency complex may be utilized, such as more than two standard deviations higher, more than three standard deviations higher, or more than four standard deviations higher, and so on. In some examples, the outlier cluster has, for example, a mean dominant frequency more than one standard deviation higher in frequency than the mean dominant frequency of all channels (ignoring sub-2 Hz frequency content), e.g., more than two standard deviations higher, e.g., more than three standard deviations higher, e.g., more than four standard deviations higher.

The establishment of a baseline cluster frequency range and subsequent detection of dominant frequencies in an outlier cluster frequency range can be performed in a variety of ways, each of which may be used alone or in combination: set-threshold analysis, bimodal distribution statistical analysis of a composite signal, single-channel temporal analysis, and/or multi-channel spatial analysis.

As shown in the example of FIG. 2, the outlier channels do not produce the higher frequency continuously. Instead, the fast firing activity is transient even for such channels. Thus, the analysis (e.g., by detector 20) may be configured to monitor every channel independently and capture data for the subset of channels that exhibit a sudden switch from their baseline frequency status to the higher dominant frequency. The common baseline spectrum is likely to be shared by most or all channels over time. However, during a local fast firing event, a small cluster of channels, which may or may not be contiguous channels, will manifest dominant frequency away from the baseline spectrum. In this way, a sudden shift of mean dominant frequency from the baseline to a higher frequency spectrum (e.g., about 2 Hz higher) in a small subset of channels (but not their neighbors) for a short duration of time will identify these channels as fast firing channels.

Set-Threshold Analysis Test

As one example of cardiac fast-firing detection, a frequency value can be provided as a frequency threshold (e.g., to processor 16 in FIG. 1) either manually as user input or via an automatic threshold value generator, and dominant frequencies of individual channels are compared against the threshold during each windowed time frame. As examples, the threshold value may be set at, e.g., 8 Hz, 9 Hz, or 10 Hz. Channels exhibiting a dominant frequency greater than the threshold value are determined to be fast-firing channels and can thus be used to anatomically localize the fast-firing activity. A frequency threshold set too low may result in false-positive determinations while a frequency threshold set too high may result in missed detection of fast-firing events.

In addition to the frequency threshold, a second threshold indicative of a minimum number of channels may also be set, again, either as a user input or via an automatic determination. A determination that a fast-firing event has occurred will then only be made when a threshold number of channels have met the dominant frequency threshold criteria during a time frame.

In other examples, other criteria may be utilized to set and/or vary the threshold value or threshold range for fast firing channels. For example, the type fibrillation (e.g., atrial and/or ventricular), patient demographics (e.g., sex, weight, height) and/or the number and distribution of sensors may be used to set or modify threshold value or threshold range.

Test Using Bimodal Distribution Statistical Analysis of a Composite Signal

As another example of cardiac fast-firing detection, a composite frequency analysis signal can be generated from the frequency analyses of the plurality of channels during the analyzed time frame, e.g., by summing or averaging the frequency analyses for all good channels, resulting in a composite analysis like those shown in graphs 52, 58, or 64. Statistical analysis using any of several known tests (e.g., those by Haldane, Larkin, Benett, Tokeshi, or Holzmann and Vollmer) can then be performed to determine whether the composite frequency plot exhibits a bimodal distribution (see FIG. 4A) after earlier showing (and/or before later showing) only a unimodal distribution (see FIGS. 3A, 5A), again ignoring frequency content below about 2 Hz. The detection of a statistically significant bimodal distribution in the composite plot (as in plot 58) can trigger the determination that a fast-firing event has occurred. Channels having a dominant frequency larger than a determined antimode frequency (e.g., the least frequent value or range between the modes) during the fast-firing event time frame(s) can be labeled as fast-firing channels and can thus be used to anatomically localize the fast-firing activity.

Single-Channel Temporal Analysis Test

As yet another example of cardiac fast-firing detection, the frequency plot of each channel (e.g., exclusive of bad channels) can be analyzed to test for changes in the dominant frequency over time, i.e., over multiple windowed time frames. Any single channel that shows substantial movement in the dominant frequency from a lower-frequency range (e.g., 3-8 Hz for the example of atrial fibrillation) to a higher-frequency range (e.g., 8-12 Hz), or vice-versa, can be labeled as a fast-firing channel during the time frame(s) the dominant frequency is in the higher-frequency range and can thus be used to anatomically localize the fast-firing activity.

Rather than a precise frequency value serving as a threshold, as in the set-threshold analysis described above, in some examples, it is the relative movement (i.e., the difference in dominant frequency values) over time that is indicative of a fast-firing episode. As with the set-threshold analysis, however, the binary determination that a fast-firing episode has occurred can be set to be made only when a threshold number of channels have been determined to have met the dominant frequency difference criteria, e.g., within a certain time period. There may also be a requirement that at least a certain number of channels (e.g., 2 channels, 3 channels, or 5 channels) are directly neighboring with each other, guaranteeing that the fast-firing detected channels appear in a cluster as may be expected of a fast-firing event. The difference criteria and/or the channel number threshold(s) can be either manually provided as user input or automatically generated, e.g., adaptively or as a default setting.

Multi-Channel Spatial Analysis Test

As still another example of cardiac fast-firing detection, the frequency plot of each channel can be compared to those of one or more spatially neighboring channels (i.e., channels for which the corresponding ECG electrode or other sensor is are in close spatial proximity to each other in terms of placement on the body of the patient) during the same time frame. Any single channel that shows substantially higher dominant frequency than a neighboring channel during the time frame can be labeled as fast-firing channel during the time frame and can thus be used to anatomically localize the fast-firing activity.

Rather than a precise frequency value serving as a threshold, as in the set-threshold analysis described above, or a temporal frequency change for the single channel, as in the single-channel temporal analysis described above, in another example, the threshold may correspond to the difference in dominant frequency values between neighboring channels within a single time period that is indicative of a fast-firing episode. As examples, the difference threshold can be set to be 4 Hz, 5 Hz, 6 Hz, or 7 Hz.

As with the other analyses, the binary determination that a fast-firing episode has occurred can be set to be made only when a threshold number of channels have been determined to have met the spatial dominant frequency difference criteria. As examples, the channel number threshold can be set to be 2 channels, 5 channels, or 10 channels. There may also be a requirement that at least a certain number of channels (e.g., 2 channels, 3 channels, or 5 channels) are directly neighboring with each other, guaranteeing that the fast-firing detected channels appear in a cluster as may be expected of a fast-firing event. The difference criteria and/or the channel number threshold(s) can be either manually provided as user input or automatically generated, e.g., adaptively or as a default setting.

Combined Fast-Firing Determination Tests

The various tests described above can in various ways be combined. For example, a channel may be determined to exhibit fast-firing activity only when it meets the criteria of a given two of the above tests, or a given three of the above tests, etc.

Anatomical Localization of Fast-Firing Activity

Figure 6:
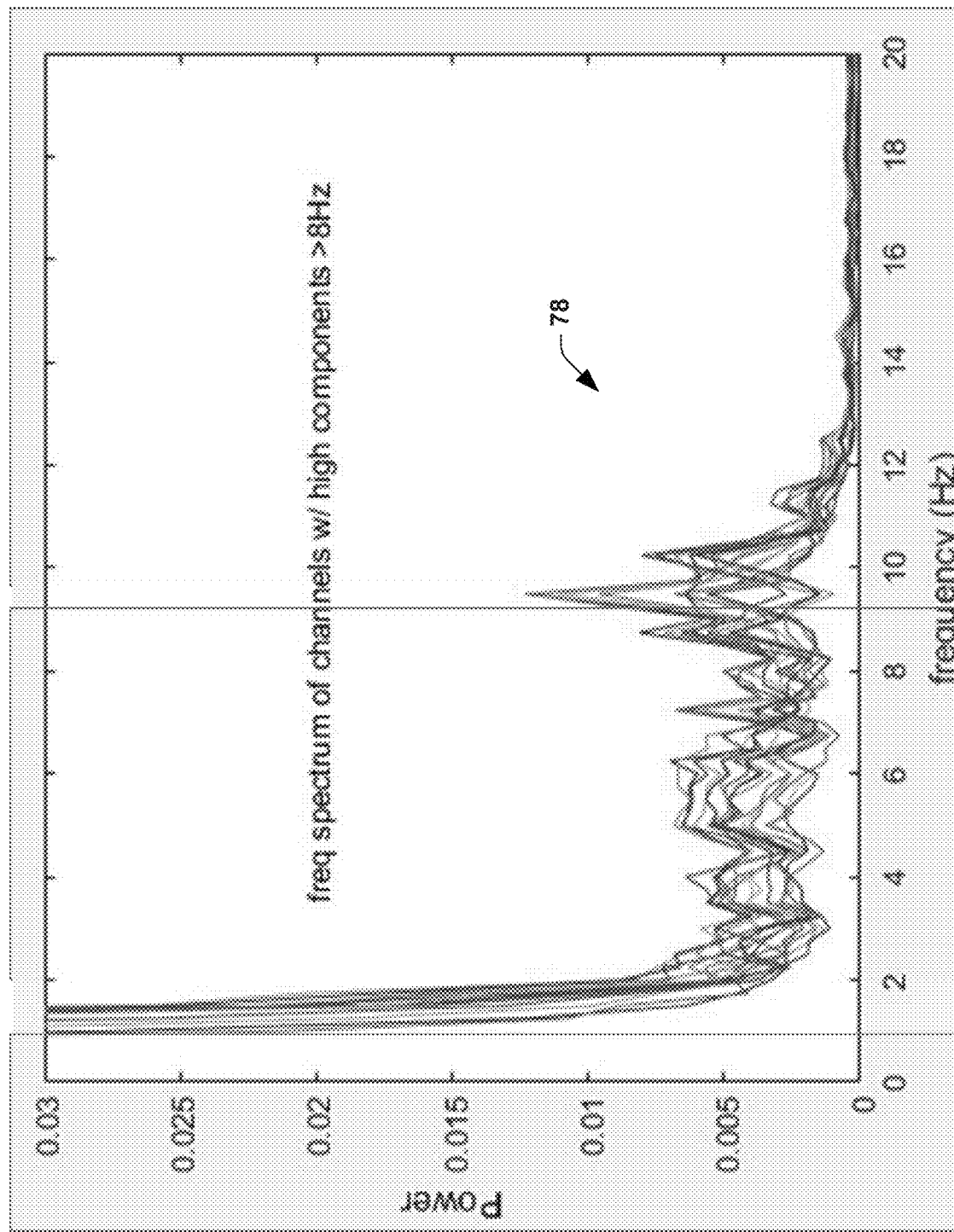
FIG. 6 depicts a frequency plot of channels determined to exhibit cardiac fast firing.
Figure 7:
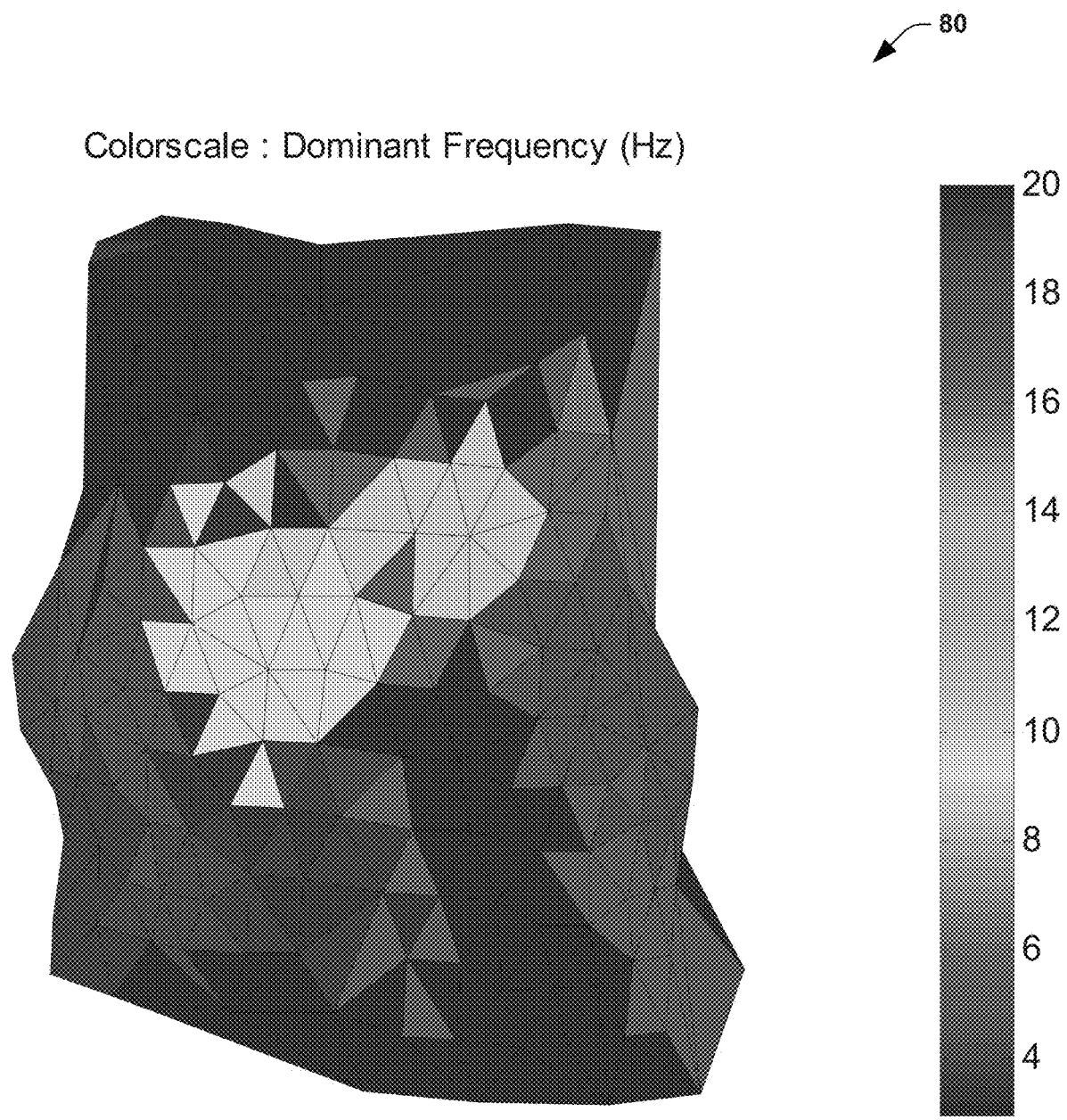
FIG. 7 depicts a thoracic graphical representation illustrating channels determined to exhibit cardiac fast firing.

Once fast-firing detection is performed, fast-firing can be localized to only those channels exhibiting fast-firing activity, as described above. FIG. 6 illustrates a frequency graph 78 with only fast-firing channels plotted. In the illustrated example, the peak dominant frequency among fast-firing channels can be seen to be at around 9.5 Hz. FIG. 7 illustrates a graphical representation 80 of the torso, like graphical representations 56, 62, 68 in the third row of FIG. 2 (and also shown in FIGS. 3C, 4C, 5C), indicating fast-firing channels as lighter-shaded triangles. The representations 80 can be displayed, as part of graphical output 36 as shown in FIG. 1, to indicate to a user where fast firing is coming from among the all analyzed channels (e.g., among 252 channels). In the illustrated example 80 of FIG. 7, one region, in the middle of the chest, exhibits the fast firing.

Figure 8:
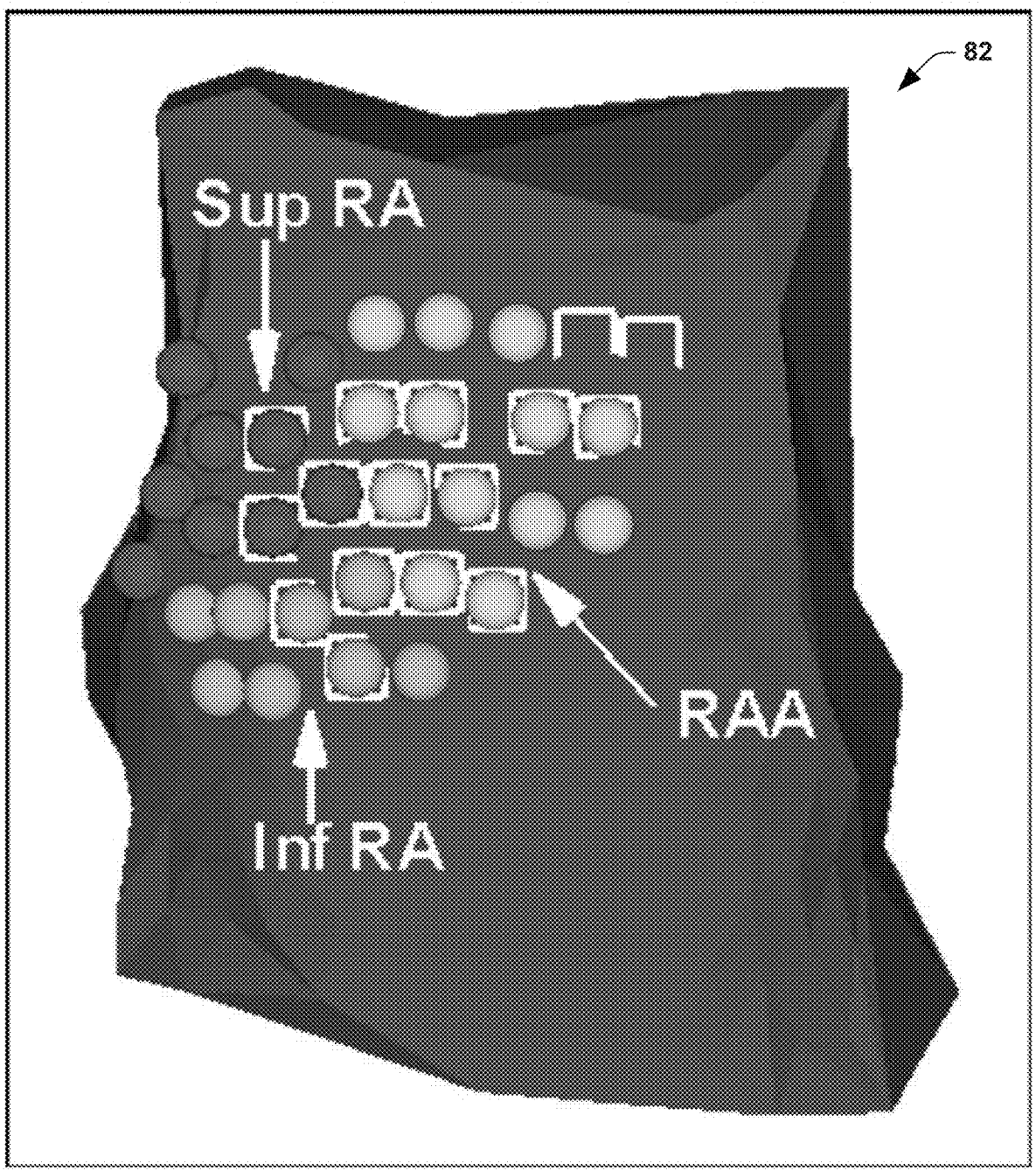
FIG. 8 depicts a thoracic graphical representation illustrating channels determined to exhibit cardiac fast firing.
Figure 9:
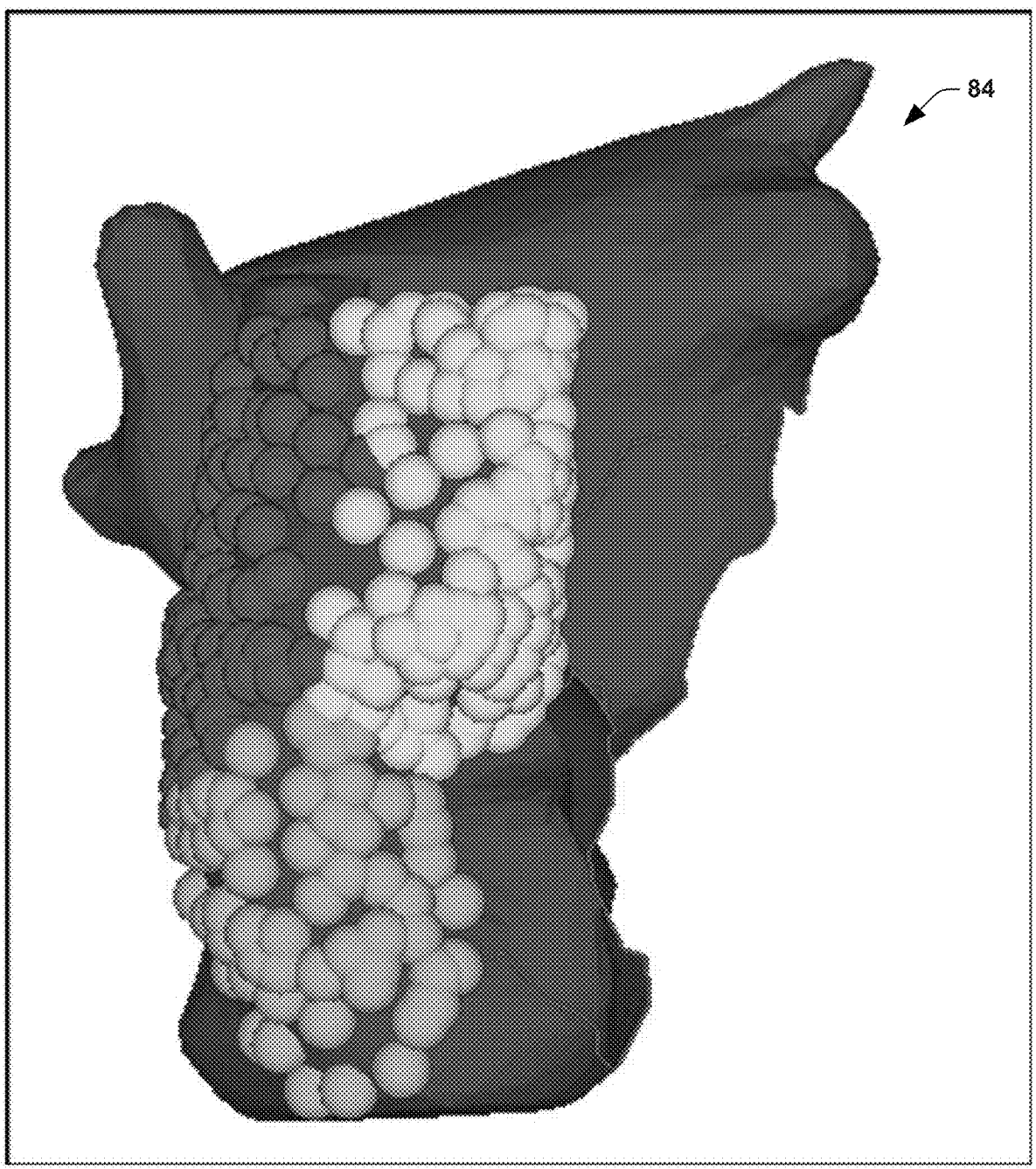
FIG. 9 depicts a graphical map of a portion of an epicardial surface illustrating regions determined to exhibit cardiac fast firing.

FIG. 8 shows another graphical representation 82 of the with channels shaded according to the anatomical regions of the heart to which those channels map according to the inverse transfer matrix $A^{-1}$, which can be computed in real time such as is described in U.S. Pat. No. 9,259,166 to Rudy et al. For example, shaded channels in the upper-left are known to correspond to the superior right atrium; shaded channels in the upper-right are known to correspond to the right atrial appendage; the remaining shaded channels, near the bottom, correspond to the inferior right atrium. Squares around certain channels indicate the channels determined to show fast-firing activity, in the present example, having a dominant frequency between 8.75 Hz and 10.25 Hz. Applying the solution to the inverse problem, which includes a transfer matrix that links certain regions on the body surface to certain region on the heart, can result in a graphical representation 84 of a portion of the cardiac anatomy, such as shown in FIG. 9, with the fast-firing regions painted using the shading scheme of FIG. 8. Because a matching table giving the mapping relationship between electrodes and cardiac surface regions is already known for the patient prior to the procedure involving the fast-firing detection, once fast firing is detected on a certain region on the body surface, the matching heart location is immediately known for the corresponding body surface location. Anatomical graphical map 84 can be displayed, as part of graphical output 36 as shown in FIG. 1, to indicate to a user the anatomical locations where fast firing originates. Because the graphical map 82 can shade the region on the cardiac anatomy (here, on the atrial anatomy) immediately based on the predetermined matching table, the fast-firing map 82 can be displayed immediately upon detection of a fast-firing event, promoting real-time use and aiding therapeutic intervention during the procedure.

The number of shaded dots in the example map of FIG. 9 are used in the illustration as a way of "painting" the anatomical regions. Various shading or visualization techniques may be used to render a graphical map based on the fast firing data.

Time-Domain QRST Detection and Removal

As disclosed herein, systems and methods disclosed herein can detect and remove QRST complexes. For example, instead of treating QRS and T as separated entities, the approach herein treats them as a single entity.

Figure 10:
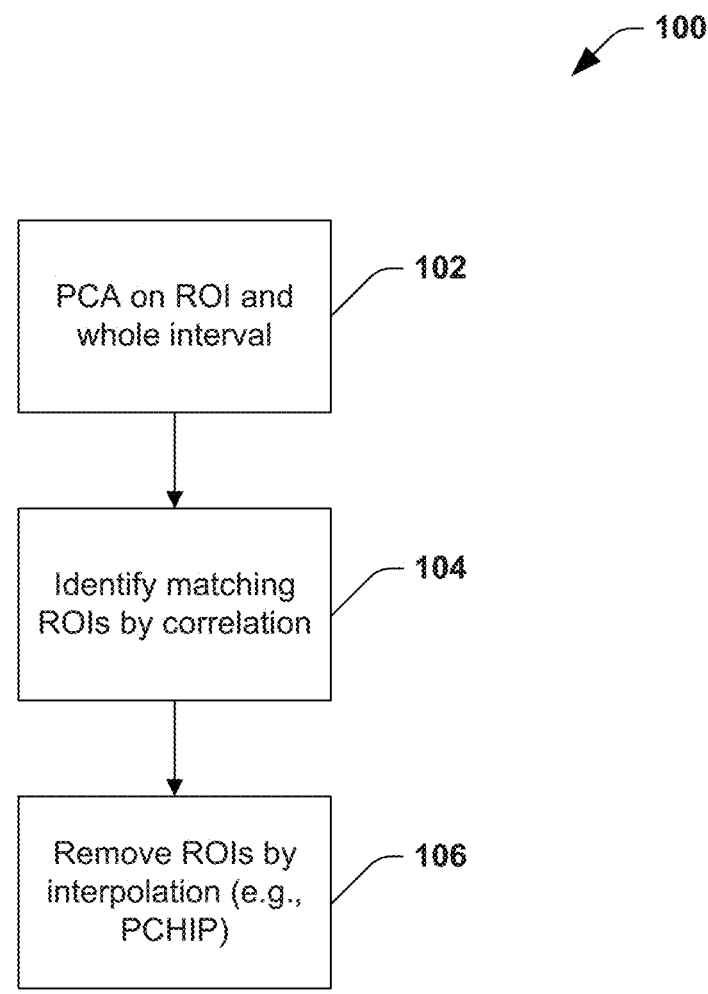
FIG. 10 is a flow diagram depicting an example method to remove QRST complexes from a cardiac waveform.

FIG. 10 is a flow diagram depicting a example time-domain method 100 to remove QRST complexes from a cardiac waveform, such as can be implemented by QRST detection and removal function 32 of FIG. 1. At 102, the QRST detection and removal function performs principal component analysis (PCA) on a selected region of interest of a cardiac waveform. The region of interest may be selected automatically or manually in response to a user input identifying an interval of signal corresponding to QRST complex. The PCA can thus be used to generate a QRST template definition. At 104, the template is applied across the time frames to identify matching regions of interest by correlation, such as by time stepping the template with respect to determine correlation coefficients. The peak correlation coefficients are used to identify potential locations in which the template matches the data. The correlation coefficients can be compared to a threshold to identify corresponding regions of interest for each of a plurality of channels.

At 106, each matching region of interest (i.e., each corresponding to a QRST complex) is removed from the cardiac waveform and interpolation (e.g., spline interpolation) is performed to connect adjacent P waves, automatically. As an example, the interpolation can be implemented as a shape-preserving PCHIP function or another spline interpolation function. Such an interpolation function keeps the interpolated values monotonic (e.g., either increasing or decreasing) based on the ending point values used for such interpolation. The QRST complex is thereby replaced in the cardiac waveform being analyzed with a substitute signal portion having no high-frequency content that would interfere with analysis of the waveform for the purposes of fast-firing detection. Baseline removal may be performed and/or bad input channels removed prior to executing the QRST detection and removal method 100.

Figure 11:
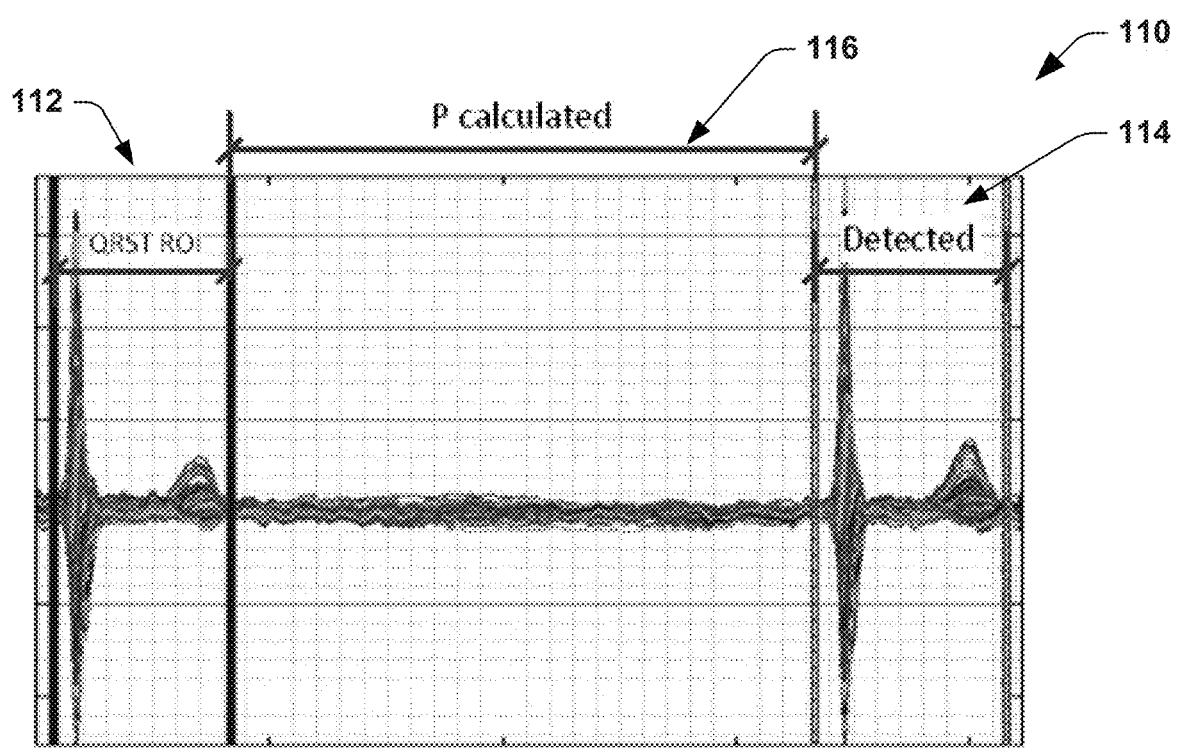
FIG. 11 depicts an example of a plurality of waveforms demonstrating identification of a P-wave based on a QRST template region.

As an example, a QRST complex can be defined to generate one template ROI, such as shown in the plot 110 of ECG data in FIG. 11. For example, a QRST template 112 is calculated and a matching ROI is detected 114 via correlation, as described above. A P wave can be automatically calculated 116 as between two adjacent ROIs, as shown in FIG. 11. As a result of using a single template for the entire QRST complex, a single set of calipers can be used to identify a region of interest.

As a simplified example, QRST detection and removal can define the QRST complex once per interval manually in response to user input. In another example, the QRST detection and removal function can implement a semi-automatic or fully automatic approach, such by automatic template matching with some standard QRST complex or a pre-selected or even pre-detected QRST.

The QRST detection and removal function (e.g., function 32, 578) operates to remove QRS and T regions of cardiac waveforms so that the residual signal magnitude in the QRS and T regions is not superior to that of P wave or cause residual signal within the P wave. To reduce artifacts caused by QRS and T signals on P signals during later filtering to obtain the frequency bandwidth of interest (e.g., about 4-15 Hz), QRST detection and removal can remove the QRST regions by interpolating with low frequency signals. This can be achieved by using approaches like monotonic cubic spline interpolation between the beginning and end of each of the QRST ROIs.

Figure 12:
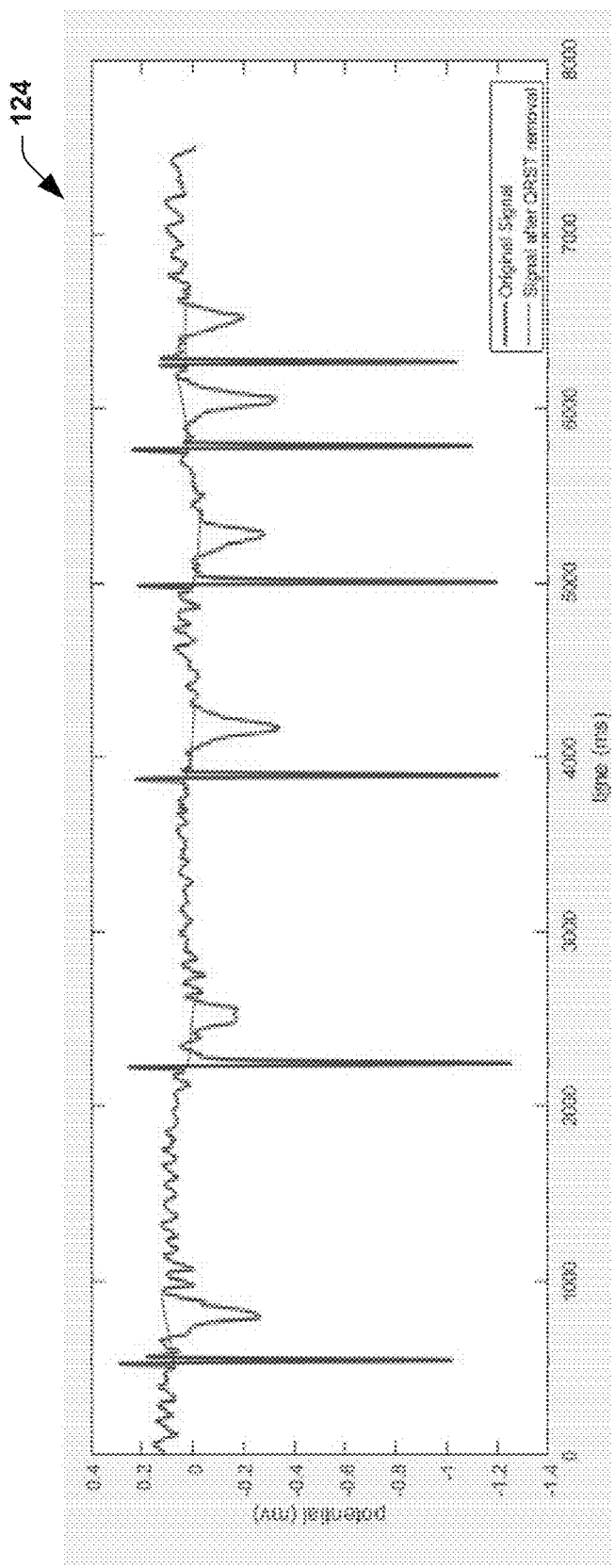
FIG. 12 depicts plots of a cardiac waveform before and after removing QRST portions.

FIG. 12 demonstrates an example case where the time-domain approach described herein succeeded at detection and removal of the QRST. As can be seen from overlain plots 124, one showing the original signal and one showing the signal after QRST removal, the QRST has been removed by spline interpolation of the QRST.

As another approach, instead of defining QRST complex and performing template matching, the QRST detection and removal function can define the P wave for one beat, and then any signal outside of the P wave will be padded. This approach can work in a beat by beat manual framework, for example.

Atrial Signals in QRST Complex

For a normal heart in sinus rhythm, there is no underlying atrial signal in the QRST complex. However, for arrhythmias like atrial fibrillation, and for atrial fast firing, atrial signals may be present during the QRST complex. To use atrial signals during the QRST complex in atrial fast firing detection, a reliable QRST subtraction approach, such as described below, may be used to remove the ventricular portion of the signals to enable analysis of the atrial signals, including those that may reside in the QRST complex.

One example to mitigate corruption of atrial signals within a region of interest (QRST) is to identify a good QRST complex during a normal sinus rhythm, with or without signal average (e.g., a "clean" QRST complex). The QRST detection and removal function can perform template matching between the clean QRST complex and the QRST complex in atrial fibrillation. By not performing any ROI averaging in the process of defining the template, the QRST detection and removal function can subtract the contribution of the clean QRST complex from each arrhythmogenic QRST complex, such that the remaining signal within the QRST interval would include atrial signals.

To reduce user interaction during map creation, the user can pick one template per procedure. For example, to define a QRST complex, the beginning and ending of the interval definition are placed at a location where signals are flat or when the heart has less activity. As baseline drift due to respiratory motion etc. can change the template profile, the baseline removal step can be performed before QRST removal. The baseline removal can also be before automatic bad-channel identification to reduce baseline drift impact on that part of the overall process.

By way of further example, the QRST detection and removal process may be implemented as a method. The method includes performing principal component analysis on a selected region of interest with respect to a plurality of ECG signals to define a QRST template. The method also includes correlating the QRST template relative to an interval of each of the plurality of ECG signals to identify matching regions of interest. The method also includes removing the identified matching regions of interest from each of the plurality of ECG signals using interpolation. For example, the region of interest is selected manually in response to a user input or the region of interest is selected automatically. As another example, the QRST template defines a single template applied to each of the ECG signals in a given time interval. As another example, the interpolation implemented by the method includes monotonic cubic spline interpolation to connect P waves together for adjacent beats. As another example, prior to removing the identified matching regions of interest, the method further includes averaging the template across the regions of interest. As another example, prior to removing the identified matching regions of interest, the method further includes adjusting the template to account for baseline drift in the ECG signals. As another example, the ECG signals include a time interval exhibiting atrial fibrillation. In this example, the method further includes: identifying a clean QRST complex during a sinus rhythm without the atrial fibrillation; performing template matching between the clean QRST complex and a QRST complex during the atrial fibrillation; and removing the clean QRST template from the ECG signals. In some examples, the method further includes automatically determining each P wave as a region between two adjacent QRST regions of interest. As another example, the method further includes detecting R-peaks for each of the ECG signals and using the detected R-peaks to locate an interval containing QRST complexes.

As disclosed, one or more non-transitory computer-readable media stores instructions to perform any variation of the method of QRST detection and removal.

Frequency-Domain QRST Detection and Removal

The QRST complex can vary greatly in length over multiple intervals (i.e., from beat to beat) over time. Frequency-domain QRST removal therefore can involve performing a frequency analysis, as described above, on an identified QRST frequency template and subtracting the resultant template frequency plot from the frequency plot of the corresponding channel. This is done channel-by-channel. For each time window, the number of QRS complexes should be provided to make sure the right amount of power contributed due to the QRS complex is removed; accordingly, the template frequency plot should not be normalized.

Acquisition, Output Displays and Treatment

Figure 13:
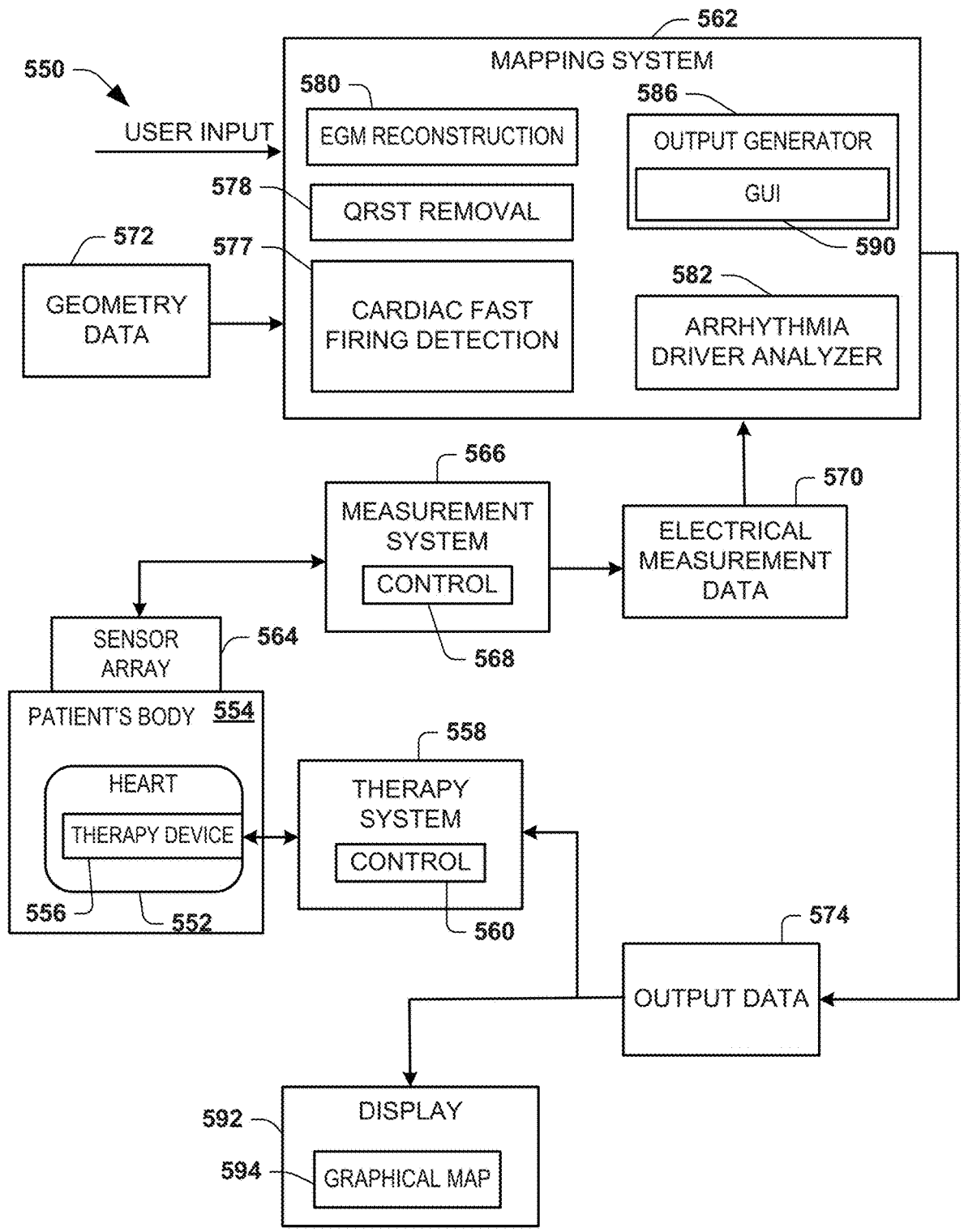
FIG. 13 depicts an example of a system that can be utilized to perform diagnostics, including cardiac fast firing detection, and/or treatment.

FIG. 13 depicts an example of a system 550 that can be utilized for generating an output to process body surface signals to characterize arrhythmogenic activity of a patient and to perform fast-firing detection. In some examples, the system 550 can generate a graphical map (e.g., a body surface map or a map on a heart model) 594 and/or display processed electrical signals. The system can also provide information in other formats to provide guidance to the user indicative of one or more of computed signal characteristics as well as information derived from such computed signal characteristics.

As disclosed herein, the system 550 has applications throughout various phases of patient care. As an example, the system can be used as part of a patient screening process (e.g., as part of a diagnostic and/or treatment planning procedure) or to perform post-treatment evaluation. Additionally, the system 550 can be utilized as part of a treatment procedure, such as to determine parameters for delivering a therapy to the patient (e.g., delivery location, amount and type of therapy). For example, a catheter, having one or more therapy delivery devices 556 affixed thereto can be inserted into the body 554 as to contact the patient's heart 552, endocardially or epicardially. Those skilled in the art will understand and appreciate various types and configurations of therapy delivery devices 556 that can be utilized, which can vary depending on the type of treatment and the procedure. For instance, the therapy device 556 can be configured to deliver electrical therapy, chemical therapy, sound wave therapy, thermal therapy or any combination thereof.

By way of further example, the therapy delivery device 556 can include one or more electrodes located at a tip of an ablation catheter configured to generate heat for ablating tissue in response to electrical signals (e.g., radiofrequency energy) supplied by a therapy system 558. In other examples, the therapy delivery device 556 can be configured to deliver cooling to perform ablation (e.g., cryogenic ablation), to deliver chemicals (e.g., drugs), ultrasound ablation, high-frequency radio frequency ablation, or a combination thereof. In still other examples, the therapy delivery device 556 can include one or more electrodes located at a tip of a pacing catheter to deliver electrical stimulation, such as for pacing the heart, in response to electrical signals (e.g., pacing current pulses) supplied by a therapy system 558. Other types of therapy can also be delivered via the therapy system 558 and the invasive therapy delivery device 556 that is positioned within the body.

As a further example, the therapy system 558 can be located external to the patient's body 554 and be configured to control therapy that is being delivered by the device 556. For instance, the therapy system 558 includes a control system (e.g., hardware and/or software) 560 that can communicate (e.g., supply) electrical signals via a conductive link electrically connected between the delivery device (e.g., one or more electrodes) 556 and the therapy system 558. The control system 560 can control parameters of the signals supplied to the device 556 (e.g., current, voltage, repetition rate, trigger delay, sensing trigger amplitude) for delivering therapy (e.g., ablation or stimulation) via the electrode(s) 554 to one or more location of the heart 552. The control system 560 can set the therapy parameters and apply stimulation based on automatic, manual (e.g., user input) or a combination of automatic and manual (e.g., semiautomatic controls). One or more sensors (not shown) can also communicate sensor information back to the therapy system 558. The position of the device 556 relative to the heart 552 can be determined and tracked intraoperatively via an imaging modality (e.g., fluoroscopy, X ray), a mapping system 562, direct vision or the like. The location of the device 556 and the therapy parameters thus can be combined to determine corresponding therapy delivery parameter.

Before, during and/or after providing a therapy via the therapy system 558, another system or subsystem can be utilized to acquire electrophysiology information for the patient. In the example of FIG. 13, a sensor array 564 includes one or more body surface electrodes that can be utilized for measuring patient electrical activity. As one example, the sensor array 564 can correspond to a high-density arrangement of body surface sensors (e.g., greater than approximately one hundred electrodes, e.g., greater than approximately two hundred electrodes, e.g., two hundred fifty-two electrodes) that are distributed over a portion of the patient's torso (e.g., thorax) for measuring electrical activity associated with the patient's heart (e.g., as part of an electrocardiographic mapping procedure). Examples of a high-density body surface non-invasive apparatus that can be used as the sensor array 564 are shown and described in U.S. Pat. No. 9,655,561 and international publication No. WO 2010/054352. Other arrangements and numbers of sensing electrodes can be used as the sensor array 564. For example, the array can be a reduced set of electrodes, which does not cover the patient's entire torso and is designed for measuring electrical activity for a particular purpose (e.g., an array of electrodes specially designed for analyzing atrial fibrillation and/or ventricular fibrillation) and/or for monitoring a predetermined spatial region of the heart. In other examples, an array having a traditional or modified 12-lead ECG or a single electrode can be implemented as the sensor array 564 to provide body surface electrical signals.

In some examples, one or more sensors may also be located on the device 556 that is inserted into the patient's body. Such sensors can be utilized separately or in conjunction with the non-invasive sensor array 564 for mapping electrical activity for an endocardial surface, such as the wall of a heart chamber, as well as for an epicardial surface. Additionally, such electrode can also be utilized to help localize the device 556 within the heart 552, which can be registered into an image or map that is generated by the system 550. Alternatively, such localization can be implemented in the absence of emitting a signal from an electrode within or on the heart 552.

In each of such example approaches for acquiring patient electrical information, including invasively, non-invasively, or a combination of invasive and non-invasive sensing, the sensor array(s) 564 provide the sensed electrical information to a corresponding measurement system 566. The measurement system 566 can include corresponding controls 568 configured to provide electrical measurement data 570 that describes electrical activity (e.g., ECG signals) detected by the sensors in the sensor array 564. For example, signal processing circuitry of the measurement system 566 can convert the measured analog signal(s) to corresponding digital information. The measurement system 566 can further process the digital information corresponding to one or more electrophysiological signals from sensor array 564 and remove non-arrhythmogenic characteristics from each such signal and to provide preprocessed data that is stored in memory as the electrical measurement data 570.

The control 568 can also be configured to control the data acquisition process for measuring electrical activity and providing the measurement data 570 (e.g., at a predefined sample rate). In some examples, the control 568 can control acquisition of measurement data 570 separately from operation of the therapy system 558 (if implemented), such as in response to a user input. In other examples, the measurement data 570 can be acquired concurrently with and in synchronization with delivering therapy by the therapy system, such as to detect electrical activity of the heart 552 that occurs in response to applying a given therapy (e.g., according to therapy parameters). For instance, appropriate time stamps can be utilized for indexing the temporal relationship between the respective measurement data 570 and therapy parameters use to deliver therapy as to facilitate the evaluation and analysis thereof.

The mapping system 562 is programmed to combine the measurement data 570 corresponding to sensed body surface electrical activity of the heart 552 to provide corresponding output data 574. The output data 574 can be represent or characterize detected ECG signals on the body surface and/or within the heart. The output data can also represent information derived from the measured signals, such as disclosed herein. The mapping system 562 can include an arrhythmia driver analyzer 582 for analyzing drivers of cardiac arrhythmia.

As one example, the mapping system 562 includes an cardiac fast firing detection function 577, such as corresponding to cardiac fast firing detector 20 (e.g., as disclosed herein with respect to FIGS. 2-9). The mapping system 562 can also include a QRST detection and removal function 578, such as corresponding to QRST detection and removal function 32 (e.g., as disclosed with respect to FIGS. 10-15). Each of the functions 577 and 578 can be applied to ECG data, demonstrated as electrical measurement data 570. As mentioned, in some examples, the cardiac fast firing detection function 577 and QRST detection and removal function 578 operate on raw ECG data (acquired, e.g., via non-invasive electrodes to measure electrical signals across a body surface) to detect cardiac (e.g., atrial) fast firing and remove QRST signals from the raw signals, respectively.

The mapping system 562 includes an output generator to provide the output data 574 to visualize on a display 592 one or more intervals of ECG signals based on the electrical measurement data acquired for the patient over one or more time intervals (e.g., before, after or during an EP procedure or treatment procedure). In an example where the sensor array 564 includes a plurality of electrodes, the output data 574 can include a selected set of channels for ECG signals measured via sensors 564 on the patient's body surface. Parameters can be set to identify a subset of signals meeting one or more user configurable parameters (e.g., via GUI 590). Some examples of output displays that can be provided by the output generator 586 are disclosed with respect to FIGS. 3C, 4C, 5C, 7, 8, and 9. The output generator thus generates the output data to display a graphical representation of time-domain plots, frequency-domain plots, channels as arranged on the torso, or regions mapped to the epicardial surface.

In some examples, computed data can be mapped to a geometric surface of a heart model. As disclosed herein, the maps can be computed based on electrical data that is acquired non-invasively via one or more electrodes in the sensor array 564 distributed on the surface of the patient's body 554.

Since the measurement system 566 can measure electrical activity of a predetermined region of the torso or the entire torso concurrently (e.g., where the sensor array 564 including a plurality of electrodes covers the entire thorax of the patient's body 554), the resulting output data (e.g., ECG signals and/or electrocardiographic maps) thus can also represent concurrent cardiac electrical data in a temporally and spatially consistent manner. The time interval for which the output data/maps are computed can be selected based on user input. Additionally or alternatively, the selected intervals can be synchronized with the application of therapy by the therapy system 558. As disclosed herein, the indication of the presence or absence of stable arrhythmogenic activity can be computed from the body surface electrical signal(s) in the absence of performing electrogram reconstruction based on patient geometry.

In other examples, where additional information may be available and geometry data 572 can be obtained, the system may include electrogram reconstruction 580 programmed to compute an inverse solution and provide corresponding reconstructed electrograms based on the process signals and the geometry data 572. For example, the geometry data 572 can correspond to a mathematical model, such as can be a generic model or a model that has been constructed based on image data obtained for the patient (e.g., via an imaging modality, such as CT, MRI, bi-plane X ray or the like) and provides spatial coordinates for the patient's heart 552 and electrodes on the sensor array. The reconstructed electrograms thus can correspond to electrocardiographic activity across a cardiac envelope, and can include static (three-dimensional at a given instant in time) and/or be dynamic (e.g., four-dimensional map that varies over time). Examples of inverse algorithms that can be utilized in the system 550 include those disclosed in U.S. Pat. Nos. 7,983,743 and 6,772,004. The EGM reconstruction 580 thus can reconstruct the body surface electrical activity measured via the sensor array 564 onto a multitude of locations on a cardiac envelope (e.g., greater than 1,000 locations, such as about 2,000 locations or more). In other examples, the mapping system 562 can compute electrical activity over a sub-region of the heart based on electrical activity measured invasively, such as via a basket catheter or other form of measurement probe (e.g., on or attached to device 556).

Parameters associated with the graphical representation, corresponding to an output visualization of the computed map, such as including selecting a time interval, a type of information that is to be presented in the visualization and the like can be selected in response to a user input via a corresponding visualization GUI 590.

Additionally, the output data 574 can be utilized by the therapy system 558, if included in the system 550. The control that is implemented can be fully automated control, semi-automated control (partially automated and responsive to a user input) or manual control based on the output data 574. In some examples, the control system 560 for the therapy system 558 can utilize the output data to control one or more therapy parameters. As an example, the control 560 can control delivery of ablation therapy to a site of the heart (e.g., epicardial or endocardial wall) based on fast firing data disclosed herein that has been determined by the function 577. For instance, the delivery of therapy can be terminated automatically in response to detecting the absence of cardiac (e.g., atrial) fast firing after a time period, or the absence of stable driver activity after a time period. In other examples, an individual user can view the map generated in the display to manually control the therapy system based on information that is visualized. Other types of therapy and devices can also be controlled based on the output data.

Figure 14:
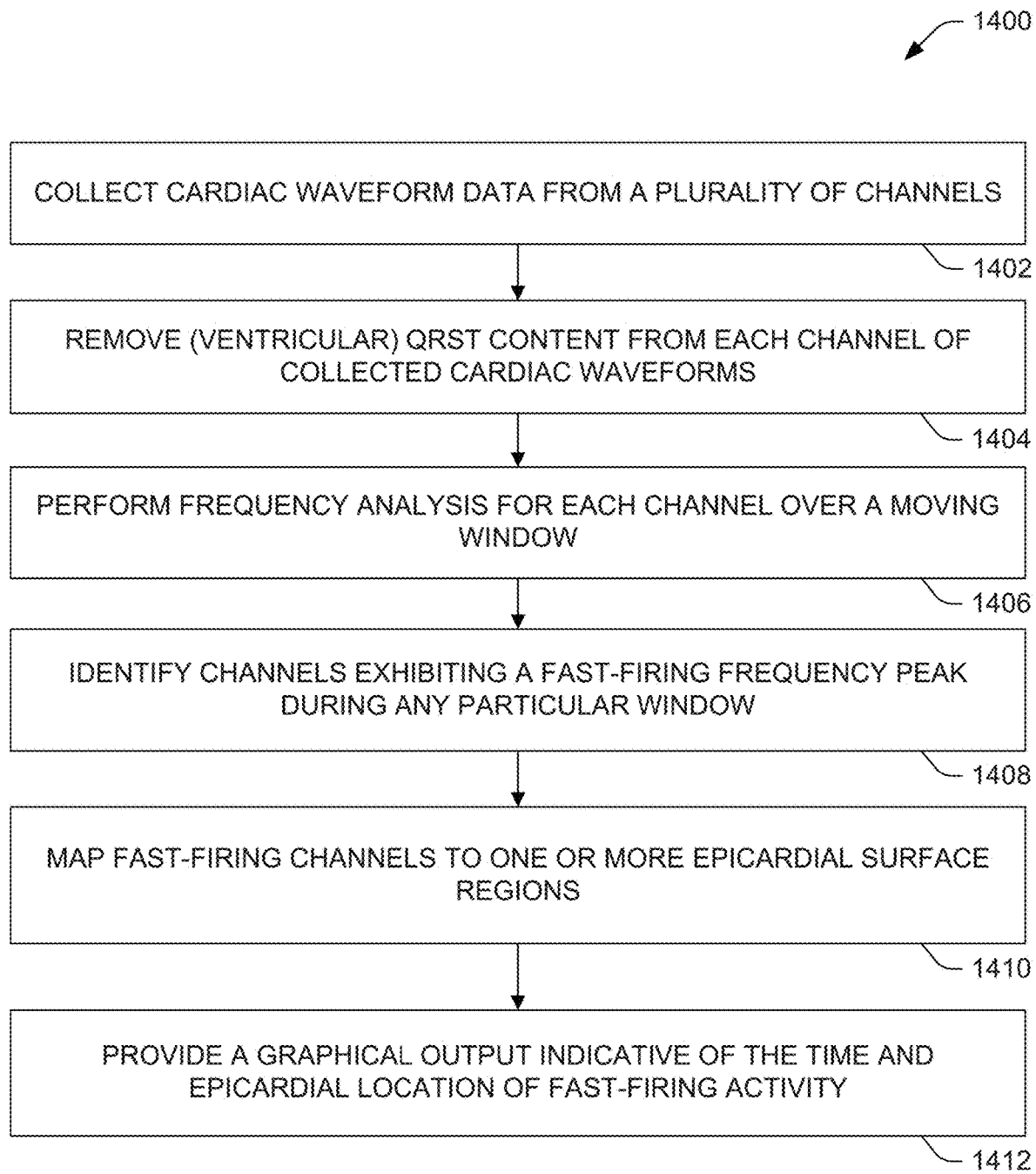
FIG. 14 is a flow diagram of an example method of cardiac fast firing detection.

FIG. 14 is a flow chart depicting an example method 1400 of detection of cardiac (e.g., atrial) fast firing activity. The method 1400 includes collecting cardiac waveform data from a plurality of channels, e.g., as may be obtained from an array of electrodes on the body surface (e.g., thorax) of a patient, e.g., in excess of one hundred channels, e.g., in excess of two hundred channels, e.g., two hundred fifty-two channels. QRST content can be removed 1404 from each channel of the collected cardiac waveforms, using, for example, one or a combination of the time-based or frequency-based methods described herein. In some examples, only ventricular QRST content is removed such that signals originating from the atrium remain in the filtered signal. A frequency analysis is performed 1406 for each channel over a moving window. As examples, the window can be, e.g., two seconds, or five seconds, or ten seconds, or twenty seconds in length. Channels exhibiting a fast-firing frequency peak during a particular window are identified 1408, e.g., using one or a combination of the tests described herein for fast-firing activity detection. A notification or warning can be given when cardiac fast-firing activity is detected. Channels identified as fast-firing in a particular time frame are mapped 1410 to one or more epicardial surface regions, and a graphical output indicative of the time and epicardial location of fast-firing activity can be provided 1412, e.g., via a visual display. The displayed graphical map can be used to guide a therapy, e.g., an ablation or a drug delivery, and/or can be used to automatically control therapy delivery, as described herein.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on."

The invention claimed is:

1. A processor-implemented method to detect cardiac fast firing activity of a heart, the method comprising:
    collecting cardiac waveform data from a measurement system configured to acquire body surface electrical measurements corresponding to a plurality of channels from body surface electrodes adapted to be placed on a patient's body surface;
    using a processor to perform frequency analysis of the collected cardiac waveform data for each of the plurality of channels over a moving window;
    using the processor to identify a proper subset of the channels exhibiting a fast-firing frequency peak within an outlier frequency cluster having a dominant frequency that is higher than a dominant frequency of a baseline frequency cluster corresponding to fibrillatory cardiac activity during a given time window within which the frequency analysis was performed; and
    using the processor to map the proper subset of channels identified as fast-firing in the given time window to one or more spatial regions of the heart.

2. The method of claim 1, wherein the frequency analysis further comprises removing QRST content from each channel of the collected cardiac waveform data.

3. The method of claim 2, wherein removing QRST content further comprises:
    performing a frequency analysis on an electrocardiographic signal derived from one of the plurality of channels to generate signal frequency plot data;
    performing a frequency analysis on an identified QRST frequency template to generate template frequency plot data;
    subtracting the template frequency plot data from the signal frequency plot data to generate frequency plot data of a QRST-removed electrocardiographic signal corresponding to the electrocardiographic signal; and
    repeating the signal frequency plot data generation and the subtraction for additional channels in the plurality of channels.

4. The method of claim 3, wherein an amount of power removed from the electrocardiographic signal in the QRST-removed electrocardiographic signal is based on a provided number of QRS complexes in the electrocardiographic signal, and wherein the template frequency plot data is not normalized.

5. The method of claim 1, further comprising generating a graphical output indicative of at least one of the time and/or anatomical location of fast-firing activity.

6. The method of claim 1, further comprising controlling delivery of a therapy based on an anatomical location of fast-firing activity that corresponds to one of the one or more spatial regions of the heart.

7. The method of claim 1, wherein the proper subset of the channels exhibiting a fast-firing frequency peak is identified based on determining respective channels from among the plurality of channels that have a mean dominant frequency that is at least one standard deviation greater than a mean dominant frequency of the baseline frequency cluster during cardiac fibrillation.

8. The method of claim 1, wherein the proper subset of the channels exhibiting a fast-firing frequency peak is identified based on:
    providing a frequency value as a frequency threshold either manually as a user input or via an automatic threshold value generator, the frequency threshold being between the dominant frequency of the outlier frequency cluster and the dominant frequency of the baseline frequency cluster;
    comparing dominant frequencies of individual channels from the among plurality of channels against the frequency threshold during the given time window; and
    determining channels from among the plurality of channels exhibiting a dominant frequency greater than the frequency threshold to be fast-firing channels within the proper subset of the channels.

9. The method of claim 8, wherein the frequency threshold is a value in the range of about 8 Hz to about 10 Hz.

10. The method of claim 8, further comprising:
providing an integer value as a channel number threshold indicative of a minimum number of channels, either manually as a user input or via an automatic determination;
determining that the fast-firing event has occurred based on a number of channels determined to be fast-firing channels exceeding the channel number threshold during the given time window.

11. The method of claim 8, further comprising anatomically localizing the fast-firing activity based on the determined fast-firing channels.

12. The method of claim 1, wherein the proper subset of the channels exhibiting a fast-firing frequency peak is identified based on:
analyzing frequency plot data of each of a plurality of given channels from among the plurality of channels to test for changes in a dominant frequency over multiple windowed time frames; and
identifying one or more of the plurality of given channels as a fast-firing channel within the proper subset of the channels during one or more time frames that the dominant frequency of the identified channel is in a higher-frequency range, based on the identified channel showing substantial movement in dominant frequency from a lower-frequency range to the higher-frequency range, or from the higher-frequency range to the lower-frequency range.

13. The method of claim 12, wherein the lower-frequency range is about 3 Hz to about 8 Hz, and wherein the higher-frequency range is about 8 Hz to about 12 Hz.

14. The method of claim 1, wherein the proper subset of the channels exhibiting a fast-firing frequency peak is identified based on comparing frequency plot data of a given channel from among the plurality of channels to frequency plot data of one or more spatially neighboring channels from among the plurality of channels during the given time window.

15. A system comprising:
a measurement system configured to acquire cardiac waveform data based on body surface electrical measurements corresponding to a plurality of channels from body surface electrodes adapted to be placed on a patient's body surface;
a processor configured to:
perform frequency analysis of the acquired cardiac waveform data for each of the plurality of channels over a moving window;
identify a proper subset of the channels exhibiting a fast-firing frequency peak within an outlier frequency cluster having a dominant frequency that is higher that a dominant frequency of a baseline frequency cluster corresponding to fibrillatory cardiac activity during a given time window within which the frequency analysis was performed; and
map the proper subset of the channels identified as fast-firing in the given time window to one or more spatial regions of a heart.

16. The system of claim 15, wherein the frequency analysis further comprises removing QRST content from each channel of the collected cardiac waveform data.

17. The system of claim 15, wherein the processor is further configured to generate a graphical output indicative of at least one of the time and/or anatomical location of fast-firing activity.

18. The system of claim 15, further comprising a therapy system configured to control delivery of a therapy based on an anatomical location of fast-firing activity that corresponds to one of the one or more spatial regions of the heart.

19. The system of claim 15, wherein the proper subset of the channels exhibiting a fast-firing frequency peak is identified based on determining respective channels from among the plurality of channels that have a mean dominant frequency that is at least one standard deviation greater than a mean dominant frequency of the baseline frequency cluster during cardiac fibrillation.

20. The system of claim 15, wherein the processor is further configured to identify the proper subset of the channels exhibiting a fast-firing frequency peak based on:
providing a frequency value as a frequency threshold either manually as a user input or via an automatic threshold value generator, the frequency threshold being between the dominant frequency of the outlier frequency cluster and the dominant frequency of the baseline frequency cluster;
comparing dominant frequencies of individual channels from among the plurality of channels against the frequency threshold during the given time window; and
determining channels from among the plurality of channels exhibiting a dominant frequency greater than the frequency threshold to be fast-firing channels within the proper subset of the channels.

21. The system of claim 20, wherein the processor is further configured to anatomically localize the fast-firing activity based on the determined fast-firing channels.

22. A processor-implemented method to detect cardiac fast firing activity of a heart, the method comprising:
using a processor to perform frequency analysis of cardiac waveform data acquired for each of a plurality of channels over a moving window;
using the processor to identify a proper subset of the channels exhibiting a fast-firing frequency peak within an outlier frequency cluster having a dominant frequency that is higher in than a dominant frequency of a baseline frequency cluster corresponding to fibrillatory cardiac activity during a given time window within which the frequency analysis was performed;
using the processor to map the proper subset of the channels identified as fast-firing in the given time window to one or more spatial regions of the heart; and
using the processor to control delivery of a therapy based on an anatomical location of fast-firing activity that corresponds to a respective one of the one or more spatial regions of the heart.

* * * * *